United States Patent [19]

Murthy et al.

[11] Patent Number: 5,935,851
[45] Date of Patent: Aug. 10, 1999

[54] TPR-CONTAINING GENES

[75] Inventors: Anita E. Murthy, Charlestown; James F. Gusella, Farmingham, both of Mass.

[73] Assignee: The General HospitalCorporation, Boston, Mass.

[21] Appl. No.: 08/879,260

[22] Filed: Jun. 19, 1997

Related U.S. Application Data

[60] Provisional application No. 60/020,204, Jun. 20, 1996.

[51] Int. Cl.$^6$ .............................. C12N 15/12; C12N 1/21; C12N 5/10; C07K 14/435
[52] U.S. Cl. .................... 435/325; 435/320.1; 435/252.3; 530/350; 536/23.5
[58] Field of Search .......................... 530/350; 435/320.1, 435/325, 252.3; 536/23.5

[56] References Cited

PUBLICATIONS

Bernards, A. et al., "Complete Human NF1 cDNA Sequence: Two Alternatively Spliced mRNAs and Absence of Expression in a Neuroblastoma Line," *DNA Cell Biol.* 11(10):727–734 (1992).

Blatch, G.L. et al., "Molecular characterization of extendin: a protein localized in extending pseudopodia," *Proc. Am. Assoc. Canc. Res.* 36:68 (Abstract No. 403) (Mar. 1995).

Carlock, L.R. and Wasmuth, J.J., "Molecular Approach to Analyzing the Human 5p Deletion Syndrome, Cri du Chat," *Somat. Cell Molec. Genet.* 11(3):267–276 (1995).

Fields, S. and Song, O., "A novel genetic system to detect protein–protein interactions," *Nature* 340:245–246 (1989).

Goebl, M. and Yanagida, M., "The TPR snap helix: a novel protein repeat motif from mitosis to transcription," *TIBS* 16:173–177 (1991).

Gyuris, J. et al., "Cdi1, a Human G1 and S Phase Protein Phosphatase That Associates with Cdk2," *Cell* 75:791–803 (1993).

Hirano, T. et al., "Snap Helix with Knob and Hole: Essential Repeats in S. pombe Nuclear Protein nuc2+," *Cell* 60:319–328 (1990).

Honoré, B. et al. "Molecular Cloning and Expression of a Transformation–sensitive Human Protein Containing the TPR Motif and Sharing Identity to the Stress–inducible Yeast Protein STI1," *J. Biol. Chem.* 267(12):8485–8491 (1992).

Lee, T.G. et al., "The 58,000–Dalton Cellular Inhibitor of the Interferon–Induced Double–Stranded RNA–Activated Protein Kinase (PKR) Is a Member of the Tetratricopeptide Repeat Family of Proteins," *Mol. Cell. Biol.* 14(4):2331–2342 (1994).

Marck, C. et al., "The TFIIIB–assembling subunit of yeast transcription factor TFIIIC has both tetratricopeptide repeats and basic helix–loop–helix motifs," *Proc. Natl. Acad. Sci. USA* 90:4027–4031 (1993).

Martin, G.A. et al., "The GAP–Related Domain of the Neurofibromatosis Type 1 Gene Product Interacts with ras p21," *Cell* 63:843–849 (1990).

McCollum, D. et al., "The pas8 Mutant of *Pichia pastoris* Exhibits the Peroxisomal Protein Import Deficiencies of Zellweger Syndrome Cells–The PAS8 Protein Binds to the COOH–Terminal Tripeptide Peroxisomal Targeting Signal, and Is a Member of the TPR Protein Family," *J. Cell Biol.* 121(4):761–774 (1993).

Narberhaus, F. et al., "Molecular Characterization of the dnak Gene Region of *Clostridium acetobutylicum*, Including grpE, dnaJ, and a New Heat Shock Gene," *J. Bacteriol.* 174(10):3290–3299 (1992).

Nicolet, C.M. and Craig, E.A., "Isolation and Characterization of STI1, a Stress–Inducible Gene from *Saccharomyces cerevisiae*," *Mol. Cell. Biol.* 9(9):3638–3646 (1989).

Ratajczak, T. et al., "The Cyclophilin Component of the Unactivated Estrogen Receptor Contains a Tetratricopeptide Repeat Domain and Shares Identity with p59 (FKBP59)," *J. Biol. Chem.* 268(18):13187–13192 (1993).

Sikorski, R.S. et al., "A Repeating Amino Acid Motif in CDC23 Defines a Family of Proteins and a New Relationship among Genes Required for Mitosis and RNA Synthesis," *Cell* 60:307–317 (1990).

Sikorski, R.S. et al., "TPR Proteins as Essential Components of the Yeast Cell Cycle," *Cold Spring Harbor Symposia on Quantitative Biology* LVI:663–673 (1991).

Steger, H.F. et al., "Import of ADP/ATP Carrier into Mitochondria: Two Receptors Act in Parallel," *J. Cell Biol.* 111:2353–2363 (1990).

Van der Leij, I. et al., "PAS10 is a tetratricopeptide–repeat protein that is essential for the import of most matrix proteins into peroxisomes of *Saccharomyces cerevisiae*," *Proc. Natl. Acad. Sci. USA* 90:11782–11786 (1993).

Warrington, J.A. et al., "Radiation Hybrid Map of 13 Loci on the Long Arm of Chromosome 5," *Genomics* 11:701–708 (1991).

Wasmuth, J.J. et al., "A Cell Hybrid and Recombinant DNA Library That Facilitate Identification of Polymorphic Loci in the Vicinity of the Huntington Disease Gene," *Am. J. Hum. Genet.* 39:397–403 (1986).

(List continued on next page.)

*Primary Examiner*—Johnny F. Railey, II
*Attorney, Agent, or Firm*—Sterne, Kessler, Goldstein & Fox, P.L.L.C.

[57] ABSTRACT

The present invention relates, in general, to novel TPR-containing genes, tpr1 and tpr2. In particular, the present invention relates to nucleic acid molecules coding for tpr1 and tpr2; purified tpr1 and tpr2 polypeptides; recombinant nucleic acid molecules; cells containing the recombinant nucleic acid molecules; antibodies having binding affinity specifically to tpr1 and tpr2 polypeptides; hybridomas containing the antibodies; nucleic acid probes for the detection of tpr1 and tpr2; a method of detecting the novel tpr1 and tpr2 nucleic acids or polypeptides in a sample; and kits containing nucleic acid probes or antibodies. Therapeutic uses for the tpr1 and tpr2 polypeptides are also provided.

12 Claims, 8 Drawing Sheets

OTHER PUBLICATIONS

Wilson, R. et al., "2.2 Mb of contiguous nucleotide sequence from chromosome III of *C. elegans*," *Nature* 368:32–38 (1994).

Xu, G. et al., "The Neurofibromatosis Type 1 Gene Encodes a Protein Related to GAP," *Cell* 62:599–608 (1990).

Zervos, A.S. et al., "Mxi1, a Protein That Specifically Interacts with Max to bind Myc–Max Recognition Sites," *Cell* 72:223–232 (1993).

Zhang, K. et al., "The crooked neck gene of Drosphila contains a motif found in a family of yeast cell cycle genes," *Genes Develop.* 5:1080–1091 (1991).

Murthy et al., DNA and Cell Biology 15(9):727–735 (1996).

```
GACCGGAGAAGCTGTGAGGTTCTTTAGCGTCACCTCCCTCACTGGGCAGCATGGGGGAGAAGTCAGAGAACTGTGGGGTTCCAGAGGATC    90
                                              *         M  G  E  K  S  E  N  C  G  V  P  E  D  L
                                                                             C
TGTTAAATGGTTTGAAGGTTACAGATACTCAGGAAGCCGAGTGTGCTGGCCCTCCAGTTCCTGATCCCAAAAATCAGCATTCCCAGAGTA    180
 L  N  G  L  K  V  T  D  T  Q  E  A  E  C  A  G  P  P  V  P  D  P  K  N  Q  H  S  Q  S  K
                                                                          H →
AGCTGCTCAGGGATGATGAGGCCCATCTCCAGGAGGACCAGGGAGAAGAGGAGTGTTTTCATGACTGCAGTGCCTCATTTGAGGAGGAGC    270
   L  L  R  D  D  E  A  H  L  Q  E  D  Q  G  E  E  E  C  F  H  D  C  S  A  S  F  E  E  P

CAGGAGCGGACAAGGTTGAGAACAAATCTAATGAAGATGTGAATTCCTCTGAACTAGATGAAGAATACCTAATAGAACTGGAAAAAAACA    360
   G  A  D  K  V  E  N  K  S  N  E  D  V  N  S  S  E  L  D  E  E  Y  L  I  E  L  E  K  N  M
   —  —  —  —  —  —  —  —  —  —  —  —  —  —  —  —  —  —  —  —  —  —  —  —  —  —  —  —  —
TGTCGGATGAAGAGAAACAGAAAAGAAGAGAAGAGAGCACTAGACTAAAGGAGGAGGGAAATGAACAGTTTAAGAAAGGAGATTATATAG    450
   S  D  E  E  K  Q  K  R  R  E  E  S  T  R  L  K  E  E  G  N  E  Q  F  K  K  G  D  Y  I  E
—  —  —  —  —  —  —  —  —  —  —  —  —  —  —  —  —  — →
AAGCTGAAAGTTCTTATAGTCGAGCCCTCGAAATGTGCCCATCCTGCTTCCAAAAGGAGAGGTCGATTCTATTTTCAAATAGAGCTGCAG    540
   A  E  S  S  Y  S  R  A  L  E  M  C  P  S  C  F  Q  K  E  R  S  I  L  F  S  N  R  A  A  A
—  —  —  —  —  —  —  —  —  —  —  —  —  —  —  —  —  —  —  —  —  —  —  —  — → —  —  —  —
CAAGGATGAAACAGGACAAGAAAGAAATGGCCATCAATGACTGCAGCAAAAGCAATTCAATTAAACCCCAGCTATATCAGGGCAATATTGA    630
   R  M  K  Q  D  K  K  E  M  A  I  N  D  C  S  K  A  I  Q  L  N  P  S  Y  I  R  A  I  L  R
—  —  —  —  —  —  —  —  —  —  —  —  —  —  —  —  —  —  —  —  —  —  —  —  — → —
GGAGAGCAGAGTTGTATGAGAAGACGGACAAGCTAGATGAAGCCCTGGAAGACTATAAATCTATATTAGAAAAAGATCCATCAATACATC    720
   R  A  E  L  Y  E  K  T  D  K  L  D  E  A  L  E  D  Y  K  S  I  L  E  K  D  P  S  I  H  Q

AAGCAAGAGAAGCTTGTATGAGATTACCTAAGCAAATTGAAGAACGTAATGAAAGACTAAAAGAAGAGATGTTAGGTAAATTAAAAGATC    810
   A  R  E  A  C  M  R  L  P  K  Q  I  E  E  R  N  E  R  L  K  E  E  M  L  G  K  L  K  D  L

TTGGGAACTTGGTTCTCCGACCTTTTGGGCTCTCCACGGAAAATTTCCAGATCAAACAGGATTCCTCTACCGGCTCGTACTCCATCAATT    900
   G  N  L  V  L  R  P  F  G  L  S  T  E  N  F  Q  I  K  Q  D  S  S  T  G  S  Y  S  I  N  F

TCGTTCAAAATCCAAATAATAACAGATAACAAAGATAACAAAAGCTTTACAAGCTGACTTGGAATTGTGTGCTGCTTGCTGTTAGCTAGG    990
   V  Q  N  P  N  N  R  *

GGAAAGGCCCTGCCAATGTTTAACTTTTAAAAGCATCTTATCTAAAAGAAAGGCTATCCAGTAGAGCCCAGTGCTCCCTTGTCCCTCTTT    1080
TATGATCAGGGTGAAATGTACTTCCTGATGTAATGAACCTAAATTTGATTTCCATTTTAAGGTGGTGTCTGTGCAGCTGGTGTCCCCGATT    1170
CTGGCTGTCCTATGTCCAGGAAGAAGCCCATTTGTTGAGGCTGACCTTCCTGATCATACACACACACAGCCCAGCAAAAGCCTCTCCTGA    1260
ACCAAACAAACCTGTTGGTTGGGAGACTGCCCAGACATGATTGATGACGGGTTCCCGCCTGCTGTCCCCTCCCTGATCACACAGCTAACG    1350
AGGCTGCCTCCAGCATTTCCTGATTTCCTCTGTGGTAATAAAAGCTTTCTGTGCTTA                                   1407
```

FIG.2

CGGCTGCCGGAGTGCCGATGCGTAATGGCCGGGCGACCCGAGCCGGACTGCTCGACGACCAAGAGGGCGAAGACAGAGACTTTCAAGGAACAAGGAAATGCATACTATGCCAAGA    120
           M  A  T  E  P  E  L  L  D  D  Q  E  A  K  R  E  A  E  T  F  K  E  Q  G  N  A  Y  Y  A  K  K

AAGATTACAATGAAGCTTATAATTATTATACAAAGGCCATAGATATGTGTCCTAAAAATGCTAGCTATTATGGTAATCGAGCAGCCACCTTGATGATGCTTGGAAGGTTCCGGGAAGCTC    240
 K  I  T  M  K  L  I  I  I  Q  R  P  *  I  C  V  L  K  N  A  S  Y  Y  G  N  R  A  A  T  L  M  M  L  G  R  F  R  E  A  L

TTGGAGATGCACAACAGTCAGTGAGGTTGGATGACAGTTTTGTCCGGGGACATCTACGAGAGGGCAAGTGCCACCTCTCTCTGGGAATGCCAGCATGTCGCAGCTTCCAGAGAC    360
 G  D  A  Q  Q  S  V  R  L  D  D  S  F  V  R  G  H  L  R  E  G  K  C  H  L  S  L  G  N  A  M  A  A  C  R  S  F  Q  R  A

CCCTAGAACTGGATCATAAAAATGCTCAGGCACAACAAGAGTTCAAGAATGCTAATGCAGTCATGGAATATGAGAAAATAGCAGAAACAGATTTTGAGAAGCGAGATTTTCGGAAGGTTG    480
 L  E  L  D  H  K  N  A  Q  Q  Q  E  F  K  N  A  N  A  V  M  E  Y  E  K  I  A  E  T  D  F  E  K  R  D  F  R  K  V  V

TTTTCTGCATGGACCGTGCCCTAGAATTTGCCCCTGCCTGCCATAGATTTAAGATCCTCAAAGCCTTCAAAATCCTCAAAGCCGAACCACAGTCTGTGGCTAGTGACA    600
 F  C  M  D  R  A  L  E  F  A  P  A  C  H  R  F  K  I  L  K  A  E  C  L  A  M  L  G  R  Y  P  E  A  Q  S  V  A  S  D  I

TTCTACGAATGATGGATTCCACCAATGCAGATGCTCTGTATGTACGAGGTCTTTGCCTTTATTGACGAAGATTGTATTGAGAAGGCAGTTCAGTTTTTCGTACAGCCTCTCAGTGCCTCTG    720
 L  R  M  D  S  T  N  A  D  A  L  Y  V  R  G  L  C  L  Y  Y  E  D  C  I  E  K  A  V  Q  F  F  V  Q  A  L  R  M  A  P  D

ACCACCGAGGCCTGCATTGCCTGCCGAAATGCCAAAGCACTCAAAGCAAAGAAGGAAGATGGGAATAAACCATTTAAGGAAGGAAATTACAAACTAGCATATGAACTGTACACGAAG    840
 H  E  K  A  C  I  A  C  R  N  A  K  A  L  K  A  K  K  E  D  G  N  K  A  F  K  E  G  N  Y  K  L  A  Y  E  L  Y  T  E  A

FIG.3A

```
CCCTGGGATAGACCCCAACAATATAAAAACAAATCCTAAACTCTACTGTAATCGGGTACCGTTAATTCCAAGCTTAGGAAACTAGATGATGCAATAGAAGACTGCACAAATGCAGTGA   960
 L  G  I  D  P  N  N  I  K  T  N  A  K  L  Y  C  N  R  G  T  V  N  S  K  L  R  K  L  D  D  A  I  E  D  C  T  N  A  V  K

AGCTTGATGACACTTACATAAAGCCTACTTGAGAAGAGCTCAGTGTTACATGACAGAACAGTATGAAGAAGCAGTACGACACTATGAAAAAGTATACCAGACAGAAAACAAAG  1080
 L  D  D  T  Y  I  K  A  Y  L  R  R  A  Q  C  Y  M  D  T  E  Q  Y  E  E  A  V  R  D  Y  E  K  V  Y  Q  T  E  K  T  K  E

AACACAAACAGCTCCTAAAAAATGCCCAGCTGGAACTGAACTGAAGAAGAGTAAGAGAAAGATTACTACAAGATTCTAGGAGTGGACAAGAATGCCTCGAGGACGAGATCAAGAAAGCTTATC 1200
 H  K  Q  L  L  K  N  A  Q  L  E  L  K  K  S  K  R  K  D  Y  Y  K  I  L  G  V  D  K  N  A  S  E  D  E  I  K  K  A  Y  R

GGAAACGGGCCTTGATGCACCATCCAGATCGGCCATAGTCGGAGCCAGTGCTCGAGGTTCAGAAGGAGGAGGAGAAGAAGTTCAAGGAAGTTGAGAGAGGCCTTTACTATCCTCTCTGATCCA 1320
 K  R  A  L  M  H  H  P  D  R  H  S  G  A  S  A  E  V  Q  K  E  E  E  K  F  K  E  V  G  E  A  F  T  I  L  S  D  P  K

AGAAAAAGACTCGCCTATGACAGGTGGACAGGACCTAGATGAGGAGGCCATGAATATGGTGATTTGATCCAACAACATATCTTCAAGGCCATTCTTTGGCGTCCTGGCGGGCTTCAGCTTTG 1440
 K  K  T  R  Y  D  S  G  Q  D  D  E  E  G  M  N  M  G  D  F  D  P  N  N  I  F  K  A  F  F  G  G  P  G  G  F  S  F  E

AAGCATCTGGTCCAGGGAATTTCTTTTTTCAATTTGGCTAATGAAGGGCAACCACCCAGAACCCAGAACCCAGAAAATGCAGATTCACTCAGTTTAATCTTGAATGTGGAAACAGTTCACCTCCTCC 1560
 A  S  G  P  G  N  F  F  F  Q  F  G  *  *

CTTCATCACGTCTCCGTGTGCTTAGAGACTTTCGTTTTCTCAGTTGGATGCCCTGCTCTGTCTCTGTGAGTGGGTGAGCAAAGGAACAATGCCGAAGACCGAGGGCAGGGCAGGGAGG 1680
CGGGGGTGGACAGGGAGGCCAGCTTGTGAATTTTTGTTTTACTGTTTAAACTTTTAATTAAAAAAGAAAAAAAAAAAAAA  1756
```

FIG.3B

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 1407 base pairs
      (B) TYPE: nucleic acid
      (C) STRANDEDNESS: both
      (D) TOPOLOGY: linear (ii) MOLECULE TYPE: cDNA (ix) FEATURE:
      (A) NAME/KEY: CDS
      (B) LOCATION: 51..926

(xi) SEQUENCE DESCRIPTION: SEQ ID NO:1:

```
GACCGGAGAA GCTGTGAGGT TCTTTAGCGT CACCTCCCTC ACTGGGCAGC ATG GGG         56
                                                        Met Gly
                                                          1

GAG AAG TCA GAG AAC TGT GGG GTT CCA GAG GAT CTG TTA AAT GGT TTG       104
Glu Lys Ser Glu Asn Cys Gly Val Pro Glu Asp Leu Leu Asn Gly Leu
          5                  10                  15

AAG GTT ACA GAT ACT CAG GAA GCC GAG TGT GCT GGC CCT CCA GTT CCT       152
Lys Val Thr Asp Thr Gln Glu Ala Glu Cys Ala Gly Pro Pro Val Pro
     20                  25                  30

GAT CCC AAA AAT CAG CAT TCC CAG AGT AAG CTG CTC AGG GAT GAT GAG       200
Asp Pro Lys Asn Gln His Ser Gln Ser Lys Leu Leu Arg Asp Asp Glu
 35                  40                  45                  50

GCC CAT CTC CAG GAG GAC CAG GGA GAA GAG GAG TGT TTT CAT GAC TGC       248
Ala His Leu Gln Glu Asp Gln Gly Glu Glu Glu Cys Phe His Asp Cys
                 55                  60                  65

AGT GCC TCA TTT GAG GAG GAG CCA GGA GCG GAC AAG GTT GAG AAC AAA       296
Ser Ala Ser Phe Glu Glu Glu Pro Gly Ala Asp Lys Val Glu Asn Lys
             70                  75                  80

TCT AAT GAA GAT GTG AAT TCC TCT GAA CTA GAT GAA GAA TAC CTA ATA       344
```

```
                Ser Asn Glu Asp Val Asn Ser Ser Glu Leu Asp Glu Glu Tyr Leu Ile
                     85                  90                  95

GAA CTG GAA AAA AAC ATG TCG GAT GAA GAG AAA CAG AAA AGA AGA GAA                392
Glu Leu Glu Lys Asn Met Ser Asp Glu Glu Lys Gln Lys Arg Arg Glu
            100                 105                 110

GAG AGC ACT AGA CTA AAG GAG GAG GGA AAT GAA CAG TTT AAG AAA GGA                440
Glu Ser Thr Arg Leu Lys Glu Glu Gly Asn Glu Gln Phe Lys Lys Gly
115                 120                 125                 130

GAT TAT ATA GAA GCT GAA AGT TCT TAT AGT CGA GCC CTC GAA ATG TGC                488
Asp Tyr Ile Glu Ala Glu Ser Ser Tyr Ser Arg Ala Leu Glu Met Cys
                135                 140                 145

CCA TCC TGC TTC CAA AAG GAG AGG TCG ATT CTA TTT TCA AAT AGA GCT                536
Pro Ser Cys Phe Gln Lys Glu Arg Ser Ile Leu Phe Ser Asn Arg Ala
            150                 155                 160

GCA GCA AGG ATG AAA CAG GAC AAG AAA GAA ATG GCC ATC AAT GAC TGC                584
Ala Ala Arg Met Lys Gln Asp Lys Lys Glu Met Ala Ile Asn Asp Cys
            165                 170                 175

AGC AAA GCA ATT CAA TTA AAC CCC AGC TAT ATC AGG GCA ATA TTG AGG                632
Ser Lys Ala Ile Gln Leu Asn Pro Ser Tyr Ile Arg Ala Ile Leu Arg
180                 185                 190

AGA GCA GAG TTG TAT GAG AAG ACG GAC AAG CTA GAT GAA GCC CTG GAA                680
Arg Ala Glu Leu Tyr Glu Lys Thr Asp Lys Leu Asp Glu Ala Leu Glu
195                 200                 205                 210

GAC TAT AAA TCT ATA TTA GAA AAA GAT CCA TCA ATA CAT CAA GCA AGA                728
Asp Tyr Lys Ser Ile Leu Glu Lys Asp Pro Ser Ile His Gln Ala Arg
                215                 220                 225

GAA GCT TGT ATG AGA TTA CCT AAG CAA ATT GAA GAA CGT AAT GAA AGA                776
Glu Ala Cys Met Arg Leu Pro Lys Gln Ile Glu Glu Arg Asn Glu Arg
            230                 235                 240

CTA AAA GAA GAG ATG TTA GGT AAA TTA AAA GAT CTT GGG AAC TTG GTT                824
Leu Lys Glu Glu Met Leu Gly Lys Leu Lys Asp Leu Gly Asn Leu Val
            245                 250                 255

CTC CGA CCT TTT GGG CTC TCC ACG GAA AAT TTC CAG ATC AAA CAG GAT                872
Leu Arg Pro Phe Gly Leu Ser Thr Glu Asn Phe Gln Ile Lys Gln Asp
260                 265                 270

TCC TCT ACC GGC TCG TAC TCC ATC AAT TTC GTT CAA AAT CCA AAT AAT                920
Ser Ser Thr Gly Ser Tyr Ser Ile Asn Phe Val Gln Asn Pro Asn Asn
275                 280                 285                 290

AAC AGA TAACAAAGAT AACAAAAGCT TTACAAGCTT ACTTGGAATT GTGTGCTGCT                 976
Asn Arg

TGCTGTTAGC TAGGGAAAG GCCCTGCCAA TGTTTAACTT TTAAAAGCAT CTTATCTAAA              1036

AGAAAGGCTA TCCAGTAGAG CCCAGTGCTC CCTTGTCCCT CTTTTATGAT CAGGGTGAAA             1096

TGTACTTCCT GATGTAATGA ACCTAATTTG ATTTCCATTT TAAGGTGGTG TCTGTGCAGC             1156

TGGTGTCCCC GATTCTGGCT GTCCTATGTC CAGGAAGAAG CCCATTTGTT GAGGCTGACC             1216

TTCCTGATCA TACACACACA CAGCCCAGCA AAAGCCTCTC CTGAACCAAA CAAACCTGTT             1276

GGTTGGGAGA CTGCCCAGAC ATGATTGATG ACGGGTTCCC GCCTGCTGTC CCCTCCCTGA             1336

TCACACAGCT AACGAGGCTG CCTCCAGCAT TTCCTGATTT CCTCTGTGGT AATAAAAGCT             1396

TTCTGTGCTT A                                                                  1407
```

(2) INFORMATION FOR SEQ ID NO:2:

(i) SEQUENCE CHARACTERISTICS:
        (A) LENGTH: 292 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Glu Lys Ser Glu Asn Cys Gly Val Pro Glu Asp Leu Leu Asn
 1               5                  10                  15

Gly Leu Lys Val Thr Asp Thr Gln Glu Ala Glu Cys Ala Gly Pro Pro
                20                  25                  30

Val Pro Asp Pro Lys Asn Gln His Ser Gln Ser Lys Leu Leu Arg Asp
                35                  40                  45

Asp Glu Ala His Leu Gln Glu Asp Gln Gly Glu Glu Glu Cys Phe His
            50                  55                  60

Asp Cys Ser Ala Ser Phe Glu Glu Glu Pro Gly Ala Asp Lys Val Glu
 65                 70                  75                  80

Asn Lys Ser Asn Glu Asp Val Asn Ser Ser Glu Leu Asp Glu Glu Tyr
                    85                  90                  95

Leu Ile Glu Leu Glu Lys Asn Met Ser Asp Glu Glu Lys Gln Lys Arg
                100                 105                 110

Arg Glu Glu Ser Thr Arg Leu Lys Glu Glu Gly Asn Glu Gln Phe Lys
                115                 120                 125

Lys Gly Asp Tyr Ile Glu Ala Glu Ser Tyr Ser Arg Ala Leu Glu
                130                 135                 140

Met Cys Pro Ser Cys Phe Gln Lys Glu Arg Ser Ile Leu Phe Ser Asn
145                 150                 155                 160

Arg Ala Ala Ala Arg Met Lys Gln Asp Lys Lys Glu Met Ala Ile Asn
                    165                 170                 175

Asp Cys Ser Lys Ala Ile Gln Leu Asn Pro Ser Tyr Ile Arg Ala Ile
                180                 185                 190

Leu Arg Arg Ala Glu Leu Tyr Glu Lys Thr Asp Lys Leu Asp Glu Ala
                195                 200                 205

Leu Glu Asp Tyr Lys Ser Ile Leu Glu Lys Asp Pro Ser Ile His Gln
                210                 215                 220

Ala Arg Glu Ala Cys Met Arg Leu Pro Lys Gln Ile Glu Glu Arg Asn
225                 230                 235                 240

Glu Arg Leu Lys Glu Glu Met Leu Gly Lys Leu Lys Asp Leu Gly Asn
                    245                 250                 255

Leu Val Leu Arg Pro Phe Gly Leu Ser Thr Glu Asn Phe Gln Ile Lys
                260                 265                 270

Gln Asp Ser Ser Thr Gly Ser Tyr Ser Ile Asn Phe Val Gln Asn Pro
                275                 280                 285

Asn Asn Asn Arg
            290
```

(2) INFORMATION FOR SEQ ID NO:3:

(i) SEQUENCE CHARACTERISTICS:
        (A) LENGTH: 1756 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 27..1478

(xi) SEQUENCE DESCRIPTION: SEQ ID NO:3:

```
CGGCTGCCGC GGAGTGCGAT GTGGTA ATG GCG GCG ACC GAG CCG GAG CTG CTC    53
                             Met Ala Ala Thr Glu Pro Glu Leu Leu
                             295                 300
```

-continued

| | | |
|---|---|---|
| GAC GAC CAA GAG GCG AAG AGG GAA GCA GAG ACT TTC AAG GAA CAA GGA<br>Asp Asp Gln Glu Ala Lys Arg Glu Ala Glu Thr Phe Lys Glu Gln Gly<br>            305                    310                  315 | 101 |
| AAT GCA TAC TAT GCC AAG AAA GAT TAC AAT GAA GCT TAT AAT TAT TAT<br>Asn Ala Tyr Tyr Ala Lys Lys Asp Tyr Asn Glu Ala Tyr Asn Tyr Tyr<br>     320                   325                  330 | 149 |
| ACA AAA GCC ATA GAT ATG TGT CCT AAA AAT GCT AGC TAT TAT GGT AAT<br>Thr Lys Ala Ile Asp Met Cys Pro Lys Asn Ala Ser Tyr Tyr Gly Asn<br>335                     340                   345 | 197 |
| CGA GCA GCC ACC TTG ATG ATG CTT GGA AGG TTC CGG GAA GCT CTT GGA<br>Arg Ala Ala Thr Leu Met Met Leu Gly Arg Phe Arg Glu Ala Leu Gly<br>350                     355                   360              365 | 245 |
| GAT GCA CAA CAG TCA GTG AGG TTG GAT GAC AGT TTT GTC CGG GGA CAT<br>Asp Ala Gln Gln Ser Val Arg Leu Asp Asp Ser Phe Val Arg Gly His<br>             370                   375                  380 | 293 |
| CTA CGA GAG GGC AAG TGC CAC CTC TCT CTG GGG AAT GCC ATG GCA GCA<br>Leu Arg Glu Gly Lys Cys His Leu Ser Leu Gly Asn Ala Met Ala Ala<br>                   385                   390                  395 | 341 |
| TGT CGC AGC TTC CAG AGA GCC CTA GAA CTG GAT CAT AAA AAT GCT CAG<br>Cys Arg Ser Phe Gln Arg Ala Leu Glu Leu Asp His Lys Asn Ala Gln<br>             400                   405                  410 | 389 |
| GCA CAA CAA GAG TTC AAG AAT GCT AAT GCA GTC ATG GAA TAT GAG AAA<br>Ala Gln Gln Glu Phe Lys Asn Ala Asn Ala Val Met Glu Tyr Glu Lys<br>     415                   420                  425 | 437 |
| ATA GCA GAA ACA GAT TTT GAG AAG CGA GAT TTT CGG AAG GTT GTT TTC<br>Ile Ala Glu Thr Asp Phe Glu Lys Arg Asp Phe Arg Lys Val Val Phe<br>430                     435                   440              445 | 485 |
| TGC ATG GAC CGT GCC CTA GAA TTT GCC CCT GCC TGC CAT CGC TTC AAA<br>Cys Met Asp Arg Ala Leu Glu Phe Ala Pro Ala Cys His Arg Phe Lys<br>             450                   455                  460 | 533 |
| ATC CTC AAG GCA GAA TGT TTA GCA ATG CTG GGT CGT TAT CCG GAA GCA<br>Ile Leu Lys Ala Glu Cys Leu Ala Met Leu Gly Arg Tyr Pro Glu Ala<br>                   465                   470                  475 | 581 |
| CAG TCT GTG GCT AGT GAC ATT CTA CGA ATG GAT TCC ACC AAT GCA GAT<br>Gln Ser Val Ala Ser Asp Ile Leu Arg Met Asp Ser Thr Asn Ala Asp<br>             480                   485                  490 | 629 |
| GCT CTG TAT GTA CGA GGT CTT TGC CTT TAT TAC GAA GAT TGT ATT GAG<br>Ala Leu Tyr Val Arg Gly Leu Cys Leu Tyr Tyr Glu Asp Cys Ile Glu<br>     495                   500                  505 | 677 |
| AAG GCA GTT CAG TTT TTC GTA CAG GCT CTC AGG ATG GCT CCT GAC CAC<br>Lys Ala Val Gln Phe Phe Val Gln Ala Leu Arg Met Ala Pro Asp His<br>510                     515                   520              525 | 725 |
| GAG AAG GCC TGC ATT GCC TGC AGA AAT GCC AAA GCA CTC AAA GCA AAG<br>Glu Lys Ala Cys Ile Ala Cys Arg Asn Ala Lys Ala Leu Lys Ala Lys<br>                   530                   535                  540 | 773 |
| AAA GAA GAT GGG AAT AAA GCA TTT AAG GAA GGA AAT TAC AAA CTA GCA<br>Lys Glu Asp Gly Asn Lys Ala Phe Lys Glu Gly Asn Tyr Lys Leu Ala<br>             545                   550                  555 | 821 |
| TAT GAA CTG TAC ACA GAA GCC CTG GGG ATA GAC CCC AAC AAT ATA AAA<br>Tyr Glu Leu Tyr Thr Glu Ala Leu Gly Ile Asp Pro Asn Asn Ile Lys<br>             560                   565                  570 | 869 |
| ACA AAT GCT AAA CTC TAC TGT AAT CGG GGT ACG GTT AAT TCC AAG CTT<br>Thr Asn Ala Lys Leu Tyr Cys Asn Arg Gly Thr Val Asn Ser Lys Leu<br>575                     580                   585 | 917 |
| AGG AAA CTA GAT GAT GCA ATA GAA GAC TGC ACA AAT GCA GTG AAG CTT<br>Arg Lys Leu Asp Asp Ala Ile Glu Asp Cys Thr Asn Ala Val Lys Leu<br>590                     595                   600              605 | 965 |
| GAT GAC ACT TAC ATA AAA GCC TAC TTG AGA AGA GCT CAG TGT TAC ATG<br>Asp Asp Thr Tyr Ile Lys Ala Tyr Leu Arg Arg Ala Gln Cys Tyr Met<br>             610                   615                  620 | 1013 |

```
GAC ACA GAA CAG TAT GAA GAA GCA GTA CGA GAC TAT GAA AAA GTA TAC       1061
Asp Thr Glu Gln Tyr Glu Glu Ala Val Arg Asp Tyr Glu Lys Val Tyr
            625                 630                 635

CAG ACA GAG AAA ACA AAA GAA CAC AAA CAG CTC CTA AAA AAT GCG CAG       1109
Gln Thr Glu Lys Thr Lys Glu His Lys Gln Leu Leu Lys Asn Ala Gln
        640                 645                 650

CTG GAA CTG AAG AAG AGT AAG AGG AAA GAT TAC TAC AAG ATT CTA GGA       1157
Leu Glu Leu Lys Lys Ser Lys Arg Lys Asp Tyr Tyr Lys Ile Leu Gly
    655                 660                 665

GTG GAC AAG AAT GCC TCT GAG GAC GAG ATC AAG AAA GCT TAT CGG AAA       1205
Val Asp Lys Asn Ala Ser Glu Asp Glu Ile Lys Lys Ala Tyr Arg Lys
670                 675                 680                 685

CGG GCC TTG ATG CAC CAT CCA GAT CGG CAT AGT GGA GCC AGT GCT GAG       1253
Arg Ala Leu Met His His Pro Asp Arg His Ser Gly Ala Ser Ala Glu
                690                 695                 700

GTT CAG AAG GAG GAG GAG AAG AAG TTC AAG GAA GTT GGA GAG GCC TTT       1301
Val Gln Lys Glu Glu Glu Lys Lys Phe Lys Glu Val Gly Glu Ala Phe
            705                 710                 715

ACT ATC CTC TCT GAT CCC AAG AAA AAG ACT CGC TAT GAC AGT GGA CAG       1349
Thr Ile Leu Ser Asp Pro Lys Lys Lys Thr Arg Tyr Asp Ser Gly Gln
        720                 725                 730

GAC CTA GAT GAG GAG GGC ATG AAT ATG GGT GAT TTT GAT CCA AAC AAT       1397
Asp Leu Asp Glu Glu Gly Met Asn Met Gly Asp Phe Asp Pro Asn Asn
    735                 740                 745

ATC TTC AAG GCA TTC TTT GGC GGT CCT GGC GGC TTC AGC TTT GAA GCA       1445
Ile Phe Lys Ala Phe Phe Gly Gly Pro Gly Gly Phe Ser Phe Glu Ala
750                 755                 760                 765

TCT GGT CCA GGG AAT TTC TTT TTT CAA TTT GGC TAATGAAGGG CAACCACCCA    1498
Ser Gly Pro Gly Asn Phe Phe Phe Gln Phe Gly
                770                 775

GAACCCAGAA AATGCAGATT CACTCAGTTT AATCTTGAAT GTGGAAACAG TTCACCTCCT    1558

CCCTTCATCA CGTCTCCGTG TGCTTAGAGC AGTTTCGTTT TCTCAGTTGG ATGCCCTGTG    1618

TCTCTGTGAG TGGGGTGGAG CAAAGGGAAC CAATGCCGAA GACCGAGGGC AGGGGAGGGA    1678

GGCGGGGGTG GACAGGGAGG CAGCTTGTGA ATTTTTGTTT TACTGTTTAA CTTTATTAAA    1738

AAAGAAAAAA AAAAAAAA                                                  1756

(2) INFORMATION FOR SEQ ID NO:4:

(i) SEQUENCE CHARACTERISTICS:
        (A) LENGTH: 484 amino acids
        (B) TYPE: amino acid
        (D) TOPOLOGY: linear (ii) MOLECULE TYPE: protein (xi) SEQUENCE DESCRIPTION: SEQ ID NO:4:

Met Ala Ala Thr Glu Pro Glu Leu Leu Asp Asp Gln Glu Ala Lys Arg
 1               5                  10                  15

Glu Ala Glu Thr Phe Lys Glu Gln Gly Asn Ala Tyr Ala Lys Lys
                20                  25                  30

Asp Tyr Asn Glu Ala Tyr Asn Tyr Tyr Thr Lys Ala Ile Asp Met Cys
            35                  40                  45

Pro Lys Asn Ala Ser Tyr Tyr Gly Asn Arg Ala Ala Thr Leu Met Met
        50                  55                  60

Leu Gly Arg Phe Arg Glu Ala Leu Gly Asp Ala Gln Gln Ser Val Arg
    65                  70                  75                  80

Leu Asp Asp Ser Phe Val Arg Gly His Leu Arg Glu Gly Lys Cys His
                85                  90                  95
```

```
Leu Ser Leu Gly Asn Ala Met Ala Ala Cys Arg Ser Phe Gln Arg Ala
            100                 105                 110

Leu Glu Leu Asp His Lys Asn Ala Gln Ala Gln Gln Glu Phe Lys Asn
            115                 120                 125

Ala Asn Ala Val Met Glu Tyr Glu Lys Ile Ala Glu Thr Asp Phe Glu
            130                 135                 140

Lys Arg Asp Phe Arg Lys Val Val Phe Cys Met Asp Arg Ala Leu Glu
145                 150                 155                 160

Phe Ala Pro Ala Cys His Arg Phe Lys Ile Leu Lys Ala Glu Cys Leu
            165                 170                 175

Ala Met Leu Gly Arg Tyr Pro Glu Ala Gln Ser Val Ala Ser Asp Ile
            180                 185                 190

Leu Arg Met Asp Ser Thr Asn Ala Asp Ala Leu Tyr Val Arg Gly Leu
            195                 200                 205

Cys Leu Tyr Tyr Glu Asp Cys Ile Glu Lys Ala Val Gln Phe Phe Val
            210                 215                 220

Gln Ala Leu Arg Met Ala Pro Asp His Glu Lys Ala Cys Ile Ala Cys
225                 230                 235                 240

Arg Asn Ala Lys Ala Leu Lys Ala Lys Lys Glu Asp Gly Asn Lys Ala
            245                 250                 255

Phe Lys Glu Gly Asn Tyr Lys Leu Ala Tyr Glu Leu Tyr Thr Glu Ala
            260                 265                 270

Leu Gly Ile Asp Pro Asn Asn Ile Lys Thr Asn Ala Lys Leu Tyr Cys
            275                 280                 285

Asn Arg Gly Thr Val Asn Ser Lys Leu Arg Lys Leu Asp Asp Ala Ile
290                 295                 300

Glu Asp Cys Thr Asn Ala Val Lys Leu Asp Asp Thr Tyr Ile Lys Ala
305                 310                 315                 320

Tyr Leu Arg Arg Ala Gln Cys Tyr Met Asp Thr Glu Gln Tyr Glu Glu
            325                 330                 335

Ala Val Arg Asp Tyr Glu Lys Val Tyr Gln Thr Glu Lys Thr Lys Glu
            340                 345                 350

His Lys Gln Leu Leu Lys Asn Ala Gln Leu Glu Leu Lys Lys Ser Lys
            355                 360                 365

Arg Lys Asp Tyr Tyr Lys Ile Leu Gly Val Asp Lys Asn Ala Ser Glu
370                 375                 380

Asp Glu Ile Lys Lys Ala Tyr Arg Lys Arg Ala Leu Met His His Pro
385                 390                 395                 400

Asp Arg His Ser Gly Ala Ser Ala Glu Val Gln Lys Glu Glu Glu Lys
            405                 410                 415

Lys Phe Lys Glu Val Gly Glu Ala Phe Thr Ile Leu Ser Asp Pro Lys
            420                 425                 430

Lys Lys Thr Arg Tyr Asp Ser Gly Gln Asp Leu Asp Glu Glu Gly Met
            435                 440                 445

Asn Met Gly Asp Phe Asp Pro Asn Asn Ile Phe Lys Ala Phe Phe Gly
            450                 455                 460

Gly Pro Gly Gly Phe Ser Phe Glu Ala Ser Gly Pro Gly Asn Phe Phe
465                 470                 475                 480

Phe Gln Phe Gly (2) INFORMATION FOR SEQ ID NO:5:

(i) SEQUENCE CHARACTERISTICS:
        (A) LENGTH: 28 base pairs
        (B) TYPE: nucleic acid
```

```
        (C) STRANDEDNESS: single
        (D) TOPOLOGY: linear (ii) MOLECULE TYPE: cDNA (xi) SEQUENCE DESCRIPTION: SEQ ID NO:5:

GGGGTCGACA CAAGGATCTC CAGACAAG                                          28

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GGGGTCGACT TATGCCACAG GTTTGTGCTC TGGAGG                                  36

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

CTTGGGAACT TGGTTCTCCG                                                    20

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

CATGTCTGGG CAGTCTCCCA AC                                                 22

(2) INFORMATION FOR SEQ ID NO:9:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GAGAGAGAGA GAGAGAGAGA ACTAGTCTCG AGTTTTTTTT TTTTTTTTTT                   50

(2) INFORMATION FOR SEQ ID NO:10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA
```

-continued (xi) SEQUENCE DESCRIPTION: SEQ ID NO:10:

AATTCGGCAC GAGGCG                                                    16

(2) INFORMATION FOR SEQ ID NO:11:

(i) SEQUENCE CHARACTERISTICS:
      (A) LENGTH: 12 base pairs
      (B) TYPE: nucleic acid
      (C) STRANDEDNESS: both
      (D) TOPOLOGY: linear (ii) MOLECULE TYPE: cDNA (xi) SEQUENCE DESCRIPTION: SEQ ID NO:11:

CGCCTCGTGC CG                                                        12

TPR-CONTAINING GENES

CROSS REFERENCE TO RELATED APPLICATIONS

This application claims the benefit of the filing date of U.S. provisional application No. 60/020,204, filed Jun. 20, 1996, now abandoned.

Statement as to Rights to Inventions Made Under Federally-Sponsored Research and Development Part of the work performed during development of this invention utilized U.S. Government funds. The U.S. Government has certain rights in this invention.

BACKGROUND OF THE INVENTION

FIELD OF THE INVENTION

The present invention relates, in general, to novel tetratricopeptide repeat (TPR)-containing genes, tpr1 and tpr2. In particular, the present invention relates to nucleic acid molecules coding for tpr1 and tpr2; purified tpr1 and tpr2 polypeptides; recombinant nucleic acid molecules; cells containing the recombinant nucleic acid molecules; antibodies having binding affinity specifically to tpr1 and tpr2 polypeptides; hybridomas containing the antibodies; nucleic acid probes for the detection of tpr1 and tpr2; a method of detecting the novel tpr1 and tpr2 nucleic acids or polypeptides in a sample; and kits containing nucleic acid probes or antibodies. Therapeutic uses for the tpr1 and tpr2 polypeptides are also provided.

BACKGROUND INFORMATION

The TPR elements were first identified in 1990 as a 34 amino acid degenerate repeating motif encoded in the genes for five fungal proteins involved in the regulation of cell division (cdc23, cdc16, nuc2/bimA/cdc27) and RNA synthesis (SSN6, SK13) (Hirano, T. etal., *Cell* 60:319–328 (1990); Sikorski, R. S. et al., *Cell* 60:307–317 (1990)). The family of TPR-containing proteins has expanded rapidly and now contains members with diverse functions including stress response (STI1/IEF SSP 3521) (Nicolet & Craig, *Mol. Cell. Biol.* 9:3638–3646 (1989); Honore, B. et al., *J. Biol. Chem.* 267:8485–8491 (1992)), interferon response (p58) (Lee, T. G. et al., *Mol. Cell. Biol.* 14:2331–2342 (1994)), mitochondrial and peroxisomal protein import (MAS70/MOM72 and PAS8/PAS10, respectively (Steger, H. F. et al., *J. Cell. Biol.* 111:2353–2363 (1990); McCollum, D. et al., *J. Cell. Biol.* 121:761–774 (1993); VanderLeu, I. et al., *Proc. Natl. Acad. Sci. USA* 90:11782–11786 (1993)), tRNA synthesis (TFC4) (Marck, C. et al., *Proc. Natl. Acad. Sci. USA* 90:4027–4031 (1993)), Drosophila neurogenesis (crn) (Zhang, K. et al., *Genes & Dev.* 5:1080 (1991)) and components of the unactivated steroid and estrogen receptors (cyclophilin, p59) (Ratajczak, T. et al., *J. Biol. Chem.* 268:13187–13192 (1993)). Despite their presence in proteins involved in a variety of cellular pathways, little is known concerning the specific function of TPR repeats although they have been proposed as mediators of protein-protein or protein-membrane interactions (Sikorski, R. S. et al., "TPR proteins as essential components of the yeast cell cycle," in Cold Spring Harbor Symp. *Quant. Biol.* LVI (1991), pp. 663–673; Goebl & Yanagida, *Trends. Biochem. Sci.* 16:173–177 (1991)).

A number of strategies based on a "two-hybrid" system have been explored as screens for protein-protein interactions (Fields & Song, *Nature* 340:245–246 (1989); Gyuris, J. et al., *Cell* 75:791–803 (1993)). These assays exploit the fact that yeast transcriptional activators are composed of two separable domains, the DNA binding domain and the transcription activation domain. Interaction between two test proteins, expressed as fusion products with these respective domains, can bring the domains together as a functional unit capable of producing transcriptional activation of reporter genes.

The present invention provides two novel human genes encoding proteins with TPR motifs which were identified while applying a protein interaction trap screen to search for gene products that associate with a portion of the GAP-related segment (GRD) of neurofibromin (Martin, G. A. et al., *Cell* 63:843–849 (1990); Xu, G. et al., *Cell* 62(3):599–608 (1990)). Interestingly, the products of these genes interact with a truncated form of the NF1 GRD but not with the intact GRD, suggesting that they may be targeted to an abnormality of protein folding. The genes tpr1 and tpr2 map to human chromosomes 5 and 17 and encode 3 and 7 TPR elements, respectively, but are not otherwise related. However, tpr2 shows similarity with p58, an inhibitor of the PKR kinase, both in its TPR repeats and in a separate region of similarity with the DnaJ protein family.

SUMMARY OF THE INVENTION

The invention provides substantially pure tpr1 and tpr2 polypeptides.

The invention further provides isolated nucleic acids which encode the tpr1 and tpr2 polypeptides.

The invention also provides nucleic acid probes for the specific detection of the presence of tpr1 and tpr2 in a sample.

The invention furter provides a method of detecting tpr1 and tpr2 nucleic acid in a sample.

The invention also provides a kit for detecting the presence of tpr1 and tpr2 nucleic acid in a sample.

The invention further provides a recombinant nucleic acid molecule comprising, 5' to 3', a promoter effective to initiate transcription in a host cell and the above-described isolated nucleic acid molecule.

The invention also provides a recombinant nucleic acid molecule comprising a vector and the above-described isolated nucleic acid molecule.

The invention further provides recombinant nucleic acid molecules comprising antisense tpr1 and tpr2 nucleic acid molecules.

The invention also provides a cell that contains the above-described recombinant nucleic acid molecule.

The invention further provides a non-human organism that contains the above-described recombinant nucleic acid molecule.

The invention also provides an antibody having binding affinity specifically to a tpr1 or tpr2 polypeptide.

The invention further provides a method of detecting a tpr1 or tpr2 polypeptide in a sample.

The invention also provides a method of measuring the amount of tpr1 or tpr2 polypeptide in a sample.

The invention further provides a diagnostic kit comprising a first container means containing the above-described antibody, and a second container means containing a conjugate comprising a binding partner of the monoclonal antibody and a label.

The invention also provides a hybridoma which produces the above described monoclonal antibody.

The invention also provides methods for therapeutic uses involving all or part of the nucleic acid sequence encoding tpr1 or tpr2.

Further objects and advantages of the present invention will be clear from the description that follows.

DEFINITIONS

In the description that follows, a number of terms used in recombinant DNA (rDNA) technology are extensively utilized. In order to provide a clear and consistent understanding of the specification and claims, including the scope to be given such terms, the following definitions are provided.

Isolated Nucleic acid Molecule. An "isolated nucleic acid molecule", as is generally understood and used herein, refers to a polymer of nucleotides, and includes but should not be limited to DNA and RNA.

DNA Segment. A DNA segment, as is generally understood and used herein, refers to a molecule comprising a linear stretch of nucleotides wherein the nucleotides are present in a sequence that can encode, through the genetic code, a molecule comprising a linear sequence of amino acid residues that is referred to as a protein, a protein fragment or a polypeptide.

Gene. A DNA sequence related to a single polypeptide chain or protein, and as used herein includes the 5' and 3' untranslated ends. The polypeptide can be encoded by a fill-length sequence or any portion of the coding sequence, so long as the functional activity of the protein is retained.

Complementary DNA (cDNA). Recombinant nucleic acid molecules synthesized by reverse transcription of messenger RNA ("mRNA").

Structural Gene. A DNA sequence that is transcribed into mRNA that is then translated into a sequence of amino acids characteristic of a specific polypeptide.

Restriction Endonuclease. A restriction endonuclease (also restriction enzyme) is an enzyme that has the capacity to recognize a specific base sequence (usually 4, 5, or 6 base pairs in length) in a DNA molecule, and to cleave the DNA molecule at every place where this sequence appears. For example, EcoRI recognizes the base sequence GAATTC/CTTAAG.

Restriction Fragment The DNA molecules produced by digestion with a restriction endonuclease are referred to as restriction fragments. Any given genome can be digested by a particular restriction endonuclease into a discrete set of restriction fragments.

Agarose Gel Electrophoresis. To detect a polymorphism in the length of restriction fragments, an analytical method for fractionating double-stranded DNA molecules on the basis of size is required. The most commonly used technique (though not the only one) for achieving such a fractionation is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. The DNA fragments of genomes can be visualized successfully. However, most genomes, including the human genome, contain far too many DNA sequences to produce a simple pattern of restriction fragments. For example, the human genome is digested into approximately 1,000,000 different DNA fragments by EcoRI. In order to visualize a small subset of these fragments, a methodology referred to as the Southern hybridization procedure can be applied.

Southern Transfer Procedure. The purpose of the Southern transfer procedure (also referred to as blotting) is to physically transfer DNA fractionated by agarose gel electrophoresis onto a nitrocellulose filter paper or another appropriate surface or method, while retaining the relative positions of DNA fragments resulting from the fractionation procedure. The methodology used to accomplish the transfer from agarose gel to nitrocellulose involves drawing the DNA from the gel into the nitrocellulose paper by capillary action.

Nucleic Acid Hybridization. Nucleic acid hybridization depends on the principle that two single-stranded nucleic acid molecules that have complementary base sequences will reform the thermodynamically favored double-stranded structure if they are mixed under the proper conditions. The double-stranded structure will be formed between two complementary single-stranded nucleic acids even if one is immobilized on a nitrocellulose filter. In the Southern hybridization procedure, the latter situation occurs. As noted previously, the DNA of the individual to be tested is digested with a restriction endonuclease, fractionated by agarose gel electrophoresis, converted to the single-stranded form, and transferred to nitrocellulose paper, making it available for reannealing to the hybridization probe.

Hybridization Probe. To visualize a particular DNA sequence in the Southern hybridization procedure, a labeled DNA molecule or hybridization probe is reacted to the fractionated DNA bound to the nitrocellulose filter. The areas on the filter that carry DNA sequences complementary to the labeled DNA probe become labeled themselves as a consequence of the reannealing reaction. The areas of the filter that exhibit such labeling are visualized. The hybridization probe is generally produced by molecular cloning of a specific DNA sequence.

Oligonucleotide or Oligomer. A molecule comprised of two or more deoxyribonucleotides or ribonucleotides, preferably more than three. Its exact size will depend on many factors, which in turn depend on the ultimate function or use of the oligonucleotide. An oligonucleotide can be derived synthetically or by cloning.

Sequence Amplification. A method for generating large amounts of a target sequence. In general, one or more amplification primers are annealed to a nucleic acid sequence. Using appropriate enzymes, sequences found adjacent to, or in between the primers are amplified.

Amplification Primer. An oligonucleotide which is capable of annealing adjacent to a target sequence and serving as an initiation point for DNA synthesis when placed under conditions in which synthesis of a primer extension product which is complementary to a nucleic acid strand is initiated.

Vector. A plasmid or phage DNA or other DNA sequence into which DNA can be inserted to be cloned. The vector can replicate autonomously in a host cell, and can be further characterized by one or a small number of endonuclease recognition sites at which such DNA sequences can be cut in a determinable fashion and into which DNA can be inserted. The vector can further contain a marker suitable for use in the identification of cells transformed with the vector. Markers, for example, are tetracycline resistance or ampicillin resistance. The words "cloning vehicle" are sometimes used for "vector."

Expression. Expression is the process by which a structural gene produces a polypeptide. It involves transcription of the gene into mRNA, and the translation of such mRNA into polypeptide(s).

Expression Vector. A vector or vehicle similar to a cloning vector but which is capable of expressing a gene which has been cloned into it, after transformation into a host. The cloned gene is usually placed under the control of (i.e., operably linked to) certain control sequences such as promoter sequences.

Expression control sequences will vary depending on whether the vector is designed to express the operably linked gene in a prokaryotic or eukaryotic host and can additionally contain transcriptional elements such as enhancer elements, termination sequences, tissue-specificity elements, and/or translational initiation and termination sites.

Functional Derivative. A "functional derivative" of a sequence, either protein or nucleic acid, is a molecule that possesses a biological activity (either functional or structural) that is substantially similar to a biological activity of the protein or nucleic acid sequence. A functional derivative of a protein can contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties can improve the molecule's solubility, absorption, biological half life, and the like. The moieties can alternatively decrease the toxicity of the molecule, eliminate or attenuate any undesirable side effect of the molecule, and the like. Moieties capable of mediating such effects are disclosed in *Remington's Pharmaceutical Sciences* (1980). Procedures for coupling such moieties to a molecule are well known in the art.

Variant. A "variant" of a protein or nucleic acid is meant to refer to a molecule substantially similar in structure and biological activity to either the protein or nucleic acid. Thus, provided that two molecules possess a common activity and can substitute for each other, they are considered variants as that term is used herein even if the composition or secondary, tertiary, or quaternary structure of one of the molecules is not identical to that found in the other, or if the amino acid or nucleotide sequence is not identical.

Allele. An "allele" is an alternative form of a gene occupying a given locus on the chromosome.

Mutation. A "mutation" is any detectable change in the genetic material which can be transmitted to daughter cells and possibly even to succeeding generations giving rise to mutant cells or mutant individuals. If the descendants of a mutant cell give rise only to somatic cells in multicellular organisms, a mutant spot or area of cells arises. Mutations in the germ line of sexually reproducing organisms can be transmitted by the gametes to the next generation resulting in an individual with the new mutant condition in both its somatic and germ cells. A mutation can be any (or a combination of) detectable, unnatural change affecting the chemical or physical constitution, mutability, replication, phenotypic function, or recombination of one or more deoxyribonucleotides; nucleotides can be added, deleted, substituted for, inverted, or transposed to new positions with and without inversion. Mutations can occur spontaneously and can be induced experimentally by application of mutagens. A mutant variation of a nucleic acid molecule results from a mutation. A mutant polypeptide can result from a mutant nucleic acid molecule.

Species. A "species" is a group of actually or potentially interbreeding natural populations. A species variation within a nucleic acid molecule or protein is a change in the nucleic acid or amino acid sequence that occurs among species and can be determined by DNA sequencing of the molecule in question.

Substantially Pure. A "substantially pure" protein or nucleic acid is a protein or nucleic acid preparation that is generally lacking in other cellular components.

BRIEF DESCRIPTION OF THE DRAWINGS

FIG. 2 DNA and deduced amino acid sequence of tpr1 (SEQ ID NO.: 1 and 2). Stop condons are indicated by asterisks. The solid arrow indicates the first nucleotides of the tpr1 clone isolated from the HeLa cell interaction library. Hatched arrows represent the TPR units. The polyadenylation signal is underlined and the last nucleotide shown is the first A of the poly tail. A G-C difference observed in cDNAs obtained from human fetal liver and brain libraries, respectively, is shown (at nucleotide 167) as is the predicted amino acid difference.

FIGS. 3A–3B. DNA and deduced amino acid sequence of tpr2 (SEQ ID NO.:3 and 4).

A) Southern analysis of genomic DNA from human/rodent somatic cell hybrids. Numbers in parentheses refer to the human chromosome present in the hybrid line.

B) PCR amplification of human/rodent somatic cell hybrids from a regional mapping panel for chromosome 5. The dH2O lane is a negative control. HHW105, HHW1064, HHW1113, HHW1118, HHW1124, and HHW1138 have been described in Warrington, J. A. et al., *Genomics* 11:701–708 (1991). HHW213 has been described in Carlock & Wasmuth, *Som. Cell. Mol. Genet.* 11(5):267–276 (1985)). A description of the remaining hybrids follows: HHW693: HHW661 chr'3 @33° C.(ts) der5p interstitial 5q (Wasmuth et al., *Am. J. Genet.* 39:397–403(1986)); HHW1405: t(5,22) (5-pter-5q11.2::22q13.3-22qter; 22pter-22q13.3::5q11.2-5qter; HHW1421: GM11570 del 5 (q15-q23.1); HHW1499: CV312 t(4;5)(q21;q31); HHW1600: (t(5;9)(5q31-9p24) balanced); HHW1107 was derived by fusing a cell line (GM7173) to UCW56-a hamster fibroblast line with a temperature sensitive mutation for the leucyl tRNA synthetase gene on 5q. The relative intensity of PCR product from HHW1124 and HHW1600 is reduced since less than 100% of the cells contain the der5.

Figure 5A:
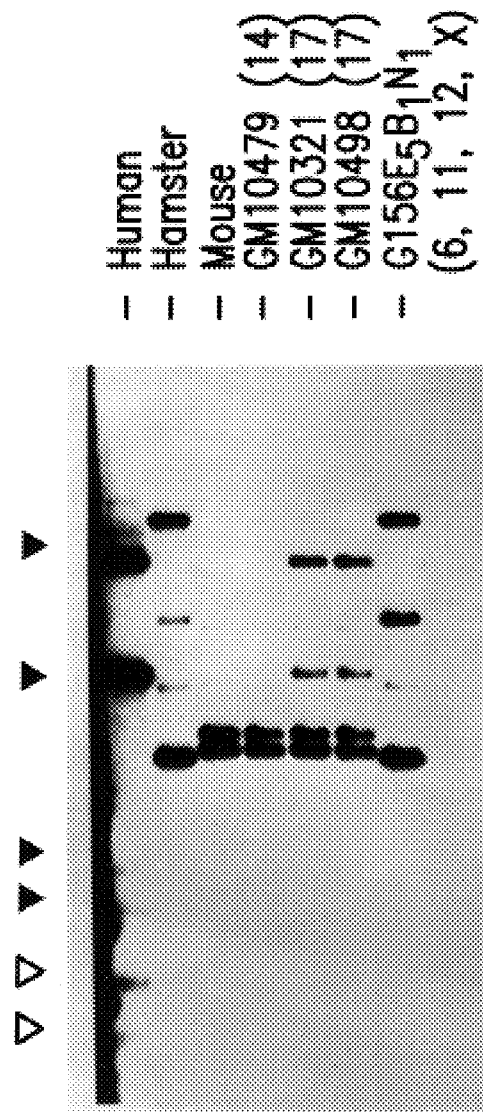
Figure 5B:
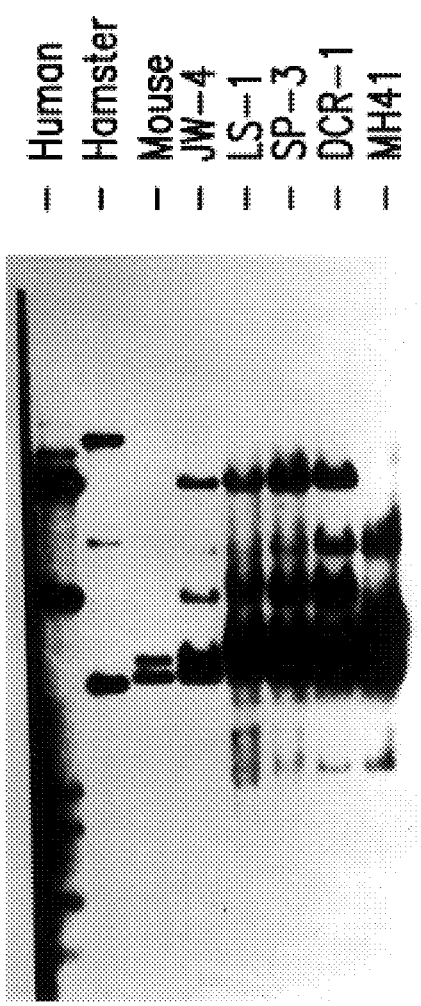

FIGS. 5A–5B. Chromosomal localization of tpr2. A: Southern analysis of genomic DNA from human/rodent somatic cell hybrids. Numbers in parentheses refer to the human chromosome(s) present in the hybrid line. B: Southern analysis of genomic DNA from chromosome 17 radiation hybrids. The lines used contain the following regions of chromosome 17: JW-4 (p13-qter), LS-1 (17center); SP3 (q11.2-qter); DCR-1 (q11.2-qter); MH41 (q23qter) (van Tuinen et al., *Genomics* 1:374–381 (1987); Menon et al., *Genomics* 5:245–49 (1989)).

Figure 1:
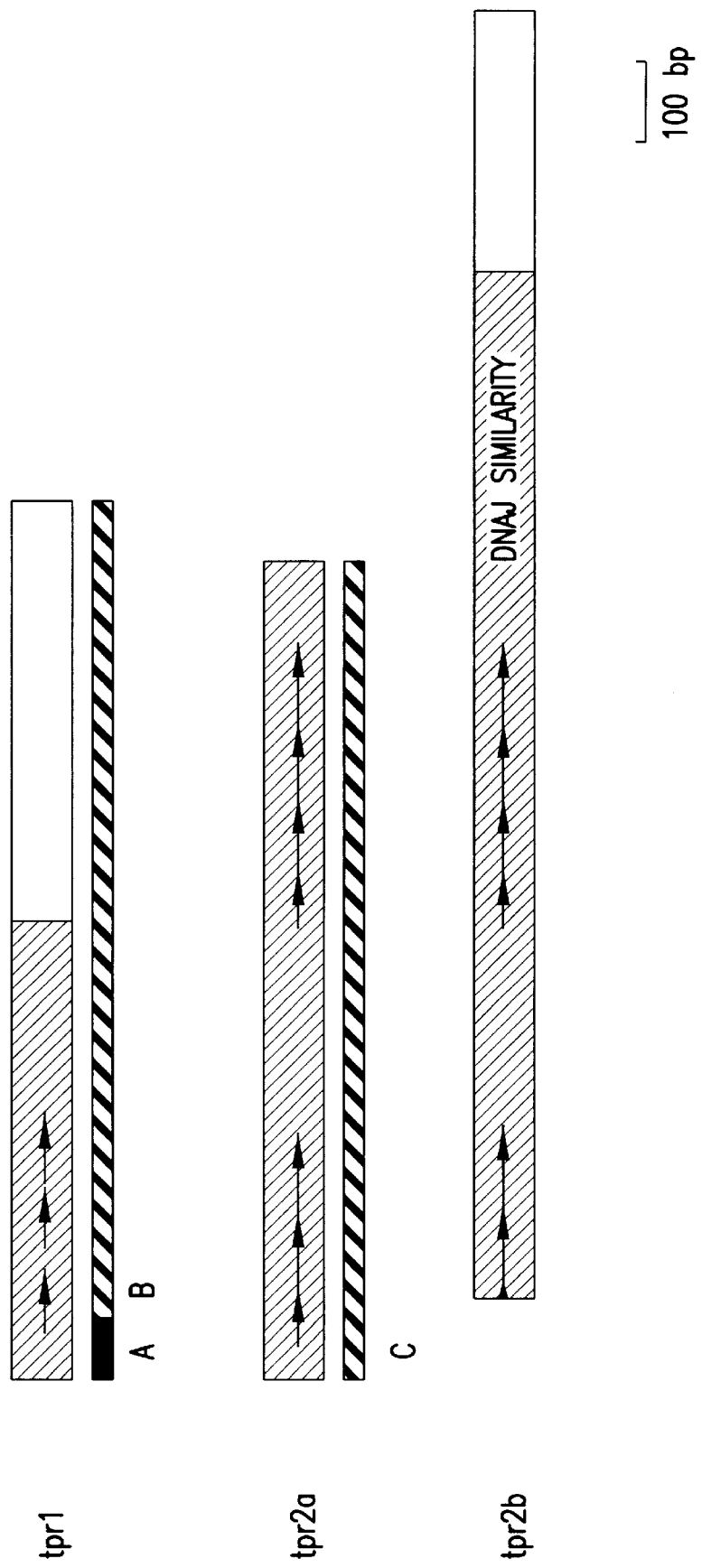
FIG. 1 Schematic illustration of the tpr1, tpr2a, and tpr2b cDNAs isolated from the HeLa cell interaction library. Shaded areas represent coding regions and stop condons are indicated by the dashed lines. The probes derived from these cDNAs are shown below them (hatched boxes) and are described herein. TPR units are represented by arrows.
Figure 6:
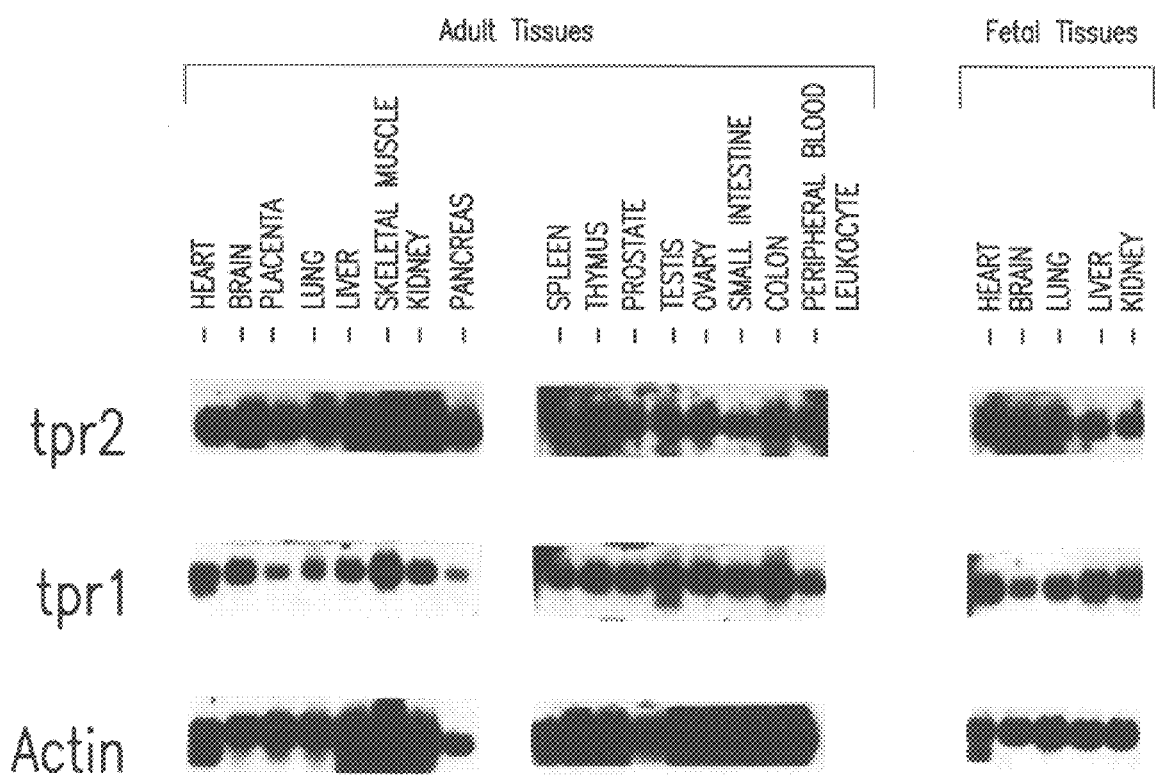

FIG. 6. Expression of tpr1 and tpr2 in human adult and fetal tissues. Northern blots (Clonetech) were hybridized with the tpr1b and tpr2 probes (FIG. 1). The acting probe was obtained from Clonetech.

DETAILED DESCRIPTION OF THE INVENTION

For purposes of clarity of disclosure, and not by way of limitation, the detailed description of the invention is divided into the following subsections:

I. Introduction

II. Isolated tpr1 and tpr2 Nucleic Acid Molecules.

III. Substantially Pure trp1 and tpr2 Polypeptides.

IV. Nucleic Acid Probes for the Specific Detection of tpr1 or tpr2 Nucleic Acid.

V. A Method of Detecting The Presence of tpr1 or tpr2 Nucleic Acid in a Sample.

VI. A Kit for Detecting the Presence of tpr1 or tpr2 Nucleic Acid in a Sample.

VII. DNA Constructs Comprising a tpr1 or tpr2 Nucleic Acid Molecule and Cells Containing These Constructs.

VIII. An Antibody Having Binding Affinity to a tpr1 or tpr2 Polypeptide and a Hybridoma Containing the Antibody.

IX. A Method of Detecting a tpr1 or tpr2 Polypeptide in a Sample.

X. A Diagnostic Kit Comprising Antibodies to a tpr1 or tpr2 Polypeptide.

XI. Diagnostic Screening and Treatment

XII. Transgenic tpr1 and tpr2 "Knock-Out" Mice

I. Introduction

The identification of two novel human genes, tpr1 and tpr2, via a two hybrid screen with a truncated neurofibromin GRD bait is described herein. The tpr1 and tpr2 predicted gene products contain 3 and 7 copies, respectively, of a degenerate, repeating amino acid motif of 34 residues, the TPR motif (Goebl & Yanagida, *Trends. Biochem. Sci.* 16:173–177 (199 1); Sikorski, R. S. et al., "TPR proteins as essential components of the yeast cell cycle," in Cold Spring Harbor *Symp. Quant. Biol.* LVI(1991), pp. 663–673). Family members generally contain between 7 and 16 copies of the TPR unit, often arranged in tandem. Although individual TPR elements show considerable divergence, an underlying pattern of amino acid identity and similarity is readily apparent. It has been proposed that arrays of TPR elements form amphipathic 25–30 residue alpha helices punctuated by a proline-induced 4 residue turn at the carboxy terminus of each repeat (Goebl & Yanagida, *Trends. Biochem. Sci.* 16:173–177 (1991); Hirano, T. et al., *Cell* 60:319–328 (1990)). In this way, the conserved amino acids Gly or Ala and Phe or Tyr at positions 8 and 24, respectively may form a "knob" and "hole" respectively such that the knob of one helix may associate with the hole of the next. This association is thought to be stabilized by the surrounding hydrophobic amino acids.

Although TPR motifs have been identified in a variety of proteins involved in diverse cellular pathways, little is known of their specific function. However, in many of the TPR-containing proteins examined thus far, amino acids within the TPR unit have been implicated in essential functional roles, suggesting that TPR elements are key in affecting the biological activity or in maintaining the stability of the proteins in which they reside. On the basis of their predicted amphipathic helical conformation, it has been predicted that TPR elements may be involved in mediating protein-protein or protein-membrane interactions (Goebl & Yanagida, *Trends. Biochem. Sci.* 16:173–177 (1991); Sikorski, R. S. et al., "TPR proteins as essential components of the yeast cell cycle," in Cold Spring *Harbor Symp. Quant. Biol.* LVI(1991), pp. 663–673). Indeed, cdc23, cdc27, and cdc16 have been shown to complex in vivo by co-immunoprecipitation and via a yeast two hybrid system (reference: Lamb et al., *EMBO J* 13:4321–4328 (1994). Thus, it is conceivable that physical interactions between TPR proteins play a role in mitosis. There is also genetic evidence that some TPR proteins interact with a class of proteins containing a different, internally repetitive domain related to the β subunit of transducin (Goebl & Yanagida, *Trends. Biochem. Sci.* 16:173–177 (1991)). The best understood example of this association is between the SSN6 and TUP1 gene products, where biochemical and genetic experiments demonstrate that the complex formed acts as a transcriptional repressor (Williams & Tumbly, *Mol. Cell. Biol.* 10:6500–6511 (1990)).

The TPR units found in the tpr1 and tpr2 predicted proteins are most similar to those found in "classIII" TPR members which have diverse roles including mitochondrial protein import, stress response, and interferon response (Lee, T. G. et al., *Mol. Cell. Biol.* 14:2331–2342 (1994); Sikorski, R. S. et al., "TPR proteins as essential components of the yeast cell cycle," in *Cold Spring Harbor Symp. Quant. Biol.* LVI(1991), pp. 663–673). The tpr1 predicted protein contains 3 tandem type III TPR units, but is not significantly similar to any other known protein outside this region. Tpr1 maps to 5q32-33.2, a region containing many human disease loci, including limb girdle muscular dystrophy, Treacher Collins syndrome, autosomal deafness, and diastrophic dysplasia. The tpr2 predicted protein is similar in structure and in sequence to p58, an inhibitor of the interferon induced cyclic AMP-independent serine/threonine kinase PKR. P58 has been shown to inhibit both the autophosphorylation and activity of PKR, most likely through a direct mechanism (Lee, T. G. et al., *Mol. Cell. Biol.* 14:2331–2342 (1994)) and it has been proposed that the TPR motifs direct the interactions between PKR and p58 or between p58 and its own regulator. Notably, it has been proposed that PKR may function as a tumor suppressor gene and that p58 has oncogenic potential. Tpr2 maps to chromosome 17q11.2-q23 and the similarity with p58 suggests the intriguing possibility that it might act as an oncogene if activated or overexpressed.

Since the tpr1 and tpr2 cDNAs are unrelated outside of their TPR domains, and since the minimal portion of tpr2 required to observe an interaction phenotype is made up entirely of tandem TPR units (FIG. 1), the TPR elements appear to be directly responsible for the observed interaction with the neurofibromin bait. It is conceivable that TPR motifs can interact promiscuously with a number of proteins but if so, TPR-containing proteins would be expected to be identified frequently in two hybrid screens. This does not appear to be the case. Moreover, studies of the cdc 23/cdc 16/cdc 27 interaction have shown that interactions between different TPR-containing proteins can be quite specific. Many class III TPR proteins have been implicated in heat shock and chaperone functions; thus, it is possible that the products of the TPR genes, isolated herein, recognize an incorrectly folded NF1 bait protein, especially since they interact preferentially with the prematurely terminating neurofibromin GRD. The failure of tpr1 and tpr2 to interact with the intact normal NF1-GRD in the two hybrid assay suggests that they do not normally bind to neurofibromin in vivo. However, the selective binding of these proteins with a truncated NF1-GRD indicates that tpr1 and tpr2 might bind with the mutant proteins typically present in patients with truncating mutations that cause NF1.

II. Isolated tpr1 and tpr2 Nucleic Acid Molecules

In one embodiment, the present invention relates to an isolated nucleic acid molecule coding for a polypeptide having an amino acid sequence corresponding to a tpr1 or tpr2 polypeptide. In one preferred embodiment, ihe isolated nucleic acid molecule comprises an tpr1 or tpr2 nucleotide sequence with greater than 70% similarity to the tpr1 or tpr2 nucleotide sequence present in SEQ ID NO:1 or 3 (preferably greater than 80%; more preferably greater than 90%). In another preferred embodiment, the isolated nucleic acid molecule comprises the tpr1 or tpr2 nucleotide sequence present in SEQ ID NO:1 or 3, respectively. In another embodiment, the isolated nucleic acid molecule encodes the tpr1 or tpr2 amino acid sequence present in SEQ ID NO:2 or 4.

Also included within the scope of this invention are the functional equivalents of the herein-described isolated nucleic acid molecules and derivatives thereof. For example, the nucleic acid sequences depicted in SEQ ID NO:1 and 3 can be altered by substitutions, additions or deletions that provide for functionally equivalent molecules. Due to the degeneracy of nucleotide coding sequences, other DNA sequences which encode substantially the same amino acid sequence as depicted in SEQ ID NO:2 and 4 can be used in the practice of the present invention. These include but are not limited to nucleotide sequences comprising all or portions of tpr1 or tpr2 nucleic acid depicted in SEQ ID NO:1 or 3 which are altered by the substitution of different codons that encode a functionally equivalent amino acid residue within the sequence, thus producing a silent change.

Such functional alterations of a given nucleic acid sequence afford an opportunity to promote secretion and/or processing of heterologous proteins encoded by foreign nucleic acid sequences fused thereto. All variations of the nucleotide sequence of the tpr1 and tpr2 genes and fragments thereof permitted by the genetic code are, therefore, included in this invention.

In addition, the nucleic acid sequence can comprise a nucleotide sequence which results from the addition, deletion or substitution of at least one nucleotide to the 5'-end and/or the 3'-end of the nucleic acid formula shown in SEQ ID NO:1 or 3 or a derivative thereof Any nucleotide or polynucleotide can be used in this regard, provided that its addition, deletion or substitution does not alter the amino acid sequence of SEQ ID NO:2 or 4 which is encoded by the nucleotide sequence. Moreover, the nucleic acid molecule of the present invention can, as necessary, have restriction endonuclease recognition sites added to its 5'-end and/or 3'-end.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

The tpr1 nucleic acids of the present invention may be used to map nucleic acid in the 5q32-33.2 human chromosome region, a region containing many human disease loci, including limb girdle muscular dystrophy. The tpr2 nucleic acid of the present invention may be used to map nucleic acid in the human chromosome 17ql 1.2-q23 region.

A. Isolation of Nucleic Acid

In one aspect of the present invention, isolated nucleic acid molecules coding for tpr1 or tpr2 polypeptide are provided. In particular, the nucleic acid molecule can be isolated from a biological sample containing human RNA or DNA.

The nucleic acid molecule can be isolated from a biological sample containing human RNA using the techniques of cDNA cloning and subtractive hybridization. The nucleic acid molecule can also be isolated from a cDNA library using a homologous probe.

The nucleic acid molecule can be isolated from a biological sample containing human genomic DNA or from a genomic library. Suitable biological samples include, but are not limited to, blood, semen and tissue. The method of obtaining the biological sample will vary depending upon the nature of the sample.

One skilled in the art will realize that the human genome can be subject to slight allelic variations between individuals. Therefore, the isolated nucleic acid molecule is also intended to include allelic variations, so long as the sequence is a functional derivative of the tpr1 or tpr2 gene. When a tpr1 or tpr2 allele does not encode the identical sequence to that found in SEQ ID NO:1 or 3, it can be isolated and identified as a tpr1 or tpr2 gene using the same techniques used herein, and especially PCR techniques to amplify the appropriate gene with primers based on the sequences disclosed herein. One skilled in the art will realize that the tpr1 and tpr2 genes are novel and are not intended to include those tpr genes present in the prior art.

One skilled in the art will realize that organisms other than humans will also contain tpr1 and tpr2 genes (for example, eukaryotes; more specifically, mammals, birds, fish, and plants; more specifically, humans, gorillas, rhesus monkeys, and chimpanzees). The invention is intended to include, but not be limited to, tpr1 and tpr2 nucleic acid molecules isolated from the above-described organisms.

B. Synthesis of Nucleic Acid

Isolated nucleic acid molecules of the present invention are also meant to include those chemically synthesized. For example, a nucleic acid molecule with the nucleotide sequence which codes for the expression product of a tpr1 or tpr2 gene can be designed and, if necessary, divided into appropriate smaller fragments. Then an oligomer which corresponds to the nucleic acid molecule, or to each of the divided fragments, can be synthesized. Such synthetic oligonucleotides can be prepared, for example, by the triester method of Matteucci et al., *J. Am. Chem. Soc.* 103:3185–3191 (1981) or by using an automated DNA synthesizer.

An oligonucleotide can be derived synthetically or by cloning. If necessary, the 5'-ends of the oligomers can be phosphorylated using T4 polynucleotide kinase. Kinasing of single strands prior to annealing or for labeling can be achieved using an excess of the enzyme. If kinasing is for the labeling of probe, the ATP can contain high specific activity radioisotopes. Then, the DNA oligomer can be subjected to annealing and ligation with T4 ligase or the like.

III. Substantially Pure tpr1 and tpr2 Polypeptides

In another embodiment, the present invention relates to substantially pure tpr1 and tpr2 polypeptide, or a functional derivative thereof. In a preferred embodiment, the polypeptide has the amino acid sequence set forth in SEQ ID NO:2 or 4, or mutant or species variation thereof, or at least 70% identity or at least 85% similarity thereof (preferably, at least 90% identity or at least 95% similarity thereof), or at least 43 contiguous amino acids thereof (preferably, at least 50 or 100 contiguous amino acids thereof).

Amino acid sequence variants of tpr1 and tpr2 can be prepared by mutations in the DNA. Such variants include, for example, deletions from, or insertions or substitutions of, residues within the amino acid sequence shown in SEQ ID NO:2 and 4. Any combination of deletion, insertion, and substitution can also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure.

While the site for introducing an amino acid sequence variation is predetermined, the mutation per se need not be predetermined. For example, to optimize the performance of a mutation at a given site, random mutagenesis can be conducted at the target codon or region and the expressed tpr1 and tpr2 variants screened for the optimal combination of desired activity. Techniques for making substitution mutations at predetermined sites in DNA having a known sequence are well known, for example, site-specific mutagenesis.

Preparation of a tpr1 or tpr2 variant in accordance herewith is preferably achieved by site-specific mutagenesis of DNA that encodes an earlier prepared variant or a nonvariant version of the protein. Site-specific mutagenesis allows the production of tpr1 and tpr2 variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA* 2:183 (1983).

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981). These phage are readily commercially available and their use is generally well known to those skilled in the art. Alternatively, plasmid vectors that contain a single-stranded phage origin of replication (Vieira et al., *Meth. Enzymol.* 153:3 (1987)) can be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci.* (USA) 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells and clones are selected that include recombinant vectors bearing the mutated sequence arrangement.

After such a clone is selected, the mutated protein region can be removed and placed in an appropriate vector for protein production, generally an expression vector of the type that can be employed for transformation of an appropriate host.

Amino acid sequence deletions generally range from about 1 to 30 residues, more preferably 1 to 10 residues, and typically are contiguous.

Amino acid sequence insertions include amino and/or carboxyl-terminal fusions of from one residue to polypeptides of essentially unrestricted length, as well as intrasequence insertions of single or multiple amino acid residues. Intrasequence insertions (i.e., insertions within the complete tpr1 or tpr2 sequence) can range generally from about 1 to 10 residues, more preferably 1 to 5.

The third group of variants are those in which at least one amino acid residue in the tpr1 or tpr2 molecule, and preferably, only one, has been removed and a different residue inserted in its place. Such substitutions preferably are made in accordance with the following Table 1 when it is desired to modulate finely the characteristics of tpr1 or tpr2.

TABLE 1

| Original Residue | Exemplary Substitutions |
| --- | --- |
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Some deletions and insertions, and substitutions are not expected to produce radical changes in the characteristics of tpr1 or tpr2. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native tpr1 or tpr2 encoding-nucleic acid, expression of the variant nucleic acid in recombinant cell culture, and, optionally, purification from the cell culture, for example, by immunoaffinity adsorption on a column (to absorb the variant by binding it to at least one remaining immune epitope). The activity of the cell lysate or purified tpr1 or tpr2 molecule variant is then screened in a suitable screening assay for the desired characteristic. For example, a change in the immunological character of the tpr1 or tpr2 molecule, such as affinity for a given antibody, is measured by a competitive type immunoassay. Changes in immunomodulation activity are measured by the appropriate assay. Modifications of such protein properties as redox or thermal stability, hydrophobicity, susceptibility to proteolytic degradation or the tendency to aggregate with carriers or into multimers are assayed by methods well known to the ordinarily skilled artisan.

A variety of methodologies known in the art can be utilized to obtain the peptide of the present invention. In one embodiment, the peptide is purified from tissues or cells which naturally produce the peptide. Alternatively, the above-described isolated nucleic acid fragments could be used to express the tpr1 or tpr2 protein in any organism. The samples of the present invention include cells, protein extracts or membrane extracts of cells, or biological fluids. The sample will vary based on the assay format, the detection method and the nature of the tissues, cells or extracts used as the sample.

Any eukaryotic organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: immunochromoto-graphy, size-exclusion chromatography, HPLC, ion-exchange chromato-graphy, and immuno-affinity chromatography.

In a preferred embodiment, the purification procedures comprise ionexchange chromatography and size exclusion chromatography. Any one of a large number of ion-exchange resins known in the art can be employed, including for example, monoQ, sepharose Q, macro-prepQ, AG1-X2, or HQ. Examples of suitable size exclusion resins include, but are not limited to, Superdex 200, Superose 12, and Sephycryl 200. Elution can be achieved with aqueous solutions of potassium chloride or sodium chloride at concentrations ranging from 0.01M to 2.0M.

IV. Nucleic Acid Probes for the Specific Detection of tpr1 and tpr2 Nucleic Acid In another embodiment, the present invention relates to a nucleic acid probe for the specific detection of the presence of tpr1 or tpr2 in a sample comprising the above-described nucleic acid molecules or at least a fragment thereof which binds under stringent conditions to tpr1 or tpr2 but not tpr genes known in the prior art. The probe is designed such that it does not have 100% homology with a similarly located TPR probe.

The nucleic acid probe can be used to probe an appropriate chromosomal or cDNA library by usual hybridization methods to obtain another nucleic acid molecule of the present invention. A chromosomal DNA or cDNA library can be prepared from appropriate cells according to recognized methods in the art (cf *Molecular Cloning: A Laboratory Manual, second edition*, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the tpr1 or tpr2. Thus, the synthesized nucleic acid probes can be used as primers in a polymerase chain reaction (PCR) carried out in accordance with recognized PCR techniques, essentially according to *PCR Protocols, A Guide to Methods and Applications*, edited by Michael et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (cf. *Molecular Cloning: A Laboratory Manual, second edition*, edited by Sambrook, Fritsch, & Maniatis, Cold Spring Harbor Laboratory, 1989).

The hybridization probes of the present invention can be labeled by standard labeling techniques such as with a radiolabel, enzyme label, fluorescent label, biotin-avidin label, chemiluminescence, and the like. After hybridization, the probes can be visualized using known methods.

The nucleic acid probes of the present invention include RNA, as well as DNA probes, such probes being generated using techniques known in the art.

In one embodiment of the above described method, a nucleic acid probe is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

V. A Method of Detecting The Presence of tpr1 or tpr2 Nucleic Acid in a Sample

In another embodiment, the present invention relates to a method of detecting the presence of tpr1 or tpr2 in a sample comprising a) contacting the sample with the above-described nucleic acid probe, under conditions such that hybridization occurs, and b) detecting the presence of the probe bound to the nucleic acid molecule. One skilled in the art would select the nucleic acid probe according to techniques known in the art as described above. Samples to be tested include but should not be limited to RNA samples of human tissue.

tpr1 or tpr2 has been found to be expressed in many cell types including brain cells. Accordingly, tpr1 or tpr2 probes can be used detect the presence of RNA from brain cells in a sample. Further, altered expression levels of tpr1 or tpr2 RNA in an individual, as compared to normal levels, can indicate the presence of disease. The tpr1 or tpr2 probes can further be used to assay cellular activity in general and specifically in brain tissue.

VI. A Kit for Detecting the Presence of tpr1 or tpr2 Nucleic Acid in a Sample In another embodiment, the present invention relates to a kit for detecting the presence of tpr1 or tpr2 in a sample comprising at least one container means having disposed therein the above-described nucleic acid probe. In a preferred embodiment, the kit further comprises other containers comprising one or more of the following: wash reagents and reagents capable of detecting the presence of bound nucleic acid probe. Examples of detection reagents include, but are not limited to radiolabelled probes, enzymatic labeled probes (horse radish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphatelbuffered saline, Trisbuffers, and the like), and containers which contain the reagents used to detect the hybridized probe, bound antibody, amplified product, or thie like.

One skilled in the art will readily recognize that the nucleic acid probes described in the present invention can readily be incorporated into one of the established kit formats which are well known in the art.

VII. DNA Constructs Comprising an tpr1 or tpr2Nucleic Acid Molecule and Cells Containing These Constructs In another embodiment, the present invention relates to a recombinant DNA molecule comprising, 5' to 3', a promoter effective to initiate transcription in a host cell and the above-described nucleic acid molecules. In another embodiment, the present invention relates to a recombinant DNA molecule comprising a vector and an above-described nucleic acid molecule.

In another embodiment, the present invention relates to a nucleic acid molecule comprising a transcriptional control region functional in a cell, a sequence complimentary to an RNA sequence encoding an amino acid sequence corresponding to the above-described polypeptide, and a transcriptional termination region functional in the cell.

Preferably, the above-described molecules are isolated and/or purified DNA molecules.

In another embodiment, the present invention relates to a cell or nonhuman organism that contains an above-described nucleic acid molecule.

In another embodiment, the peptide is purified from cells which have been altered to express the peptide.

As used herein, a cell is said to be "altered to express a desired peptide" when the cell, through genetic manipulation, is made to produce a protein which it normally does not produce or which the cell normally produces at low levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression can vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding an tpr1 or tpr2 gene can be obtained by the above-described methods. This region can be retained for its transcriptional termination regulatory sequences, such as termination and polyadenylation. Thus, by retaining the 3'-region naturally contiguous to the DNA sequence encoding an tpr1 or tpr2 gene, the transcriptional termination signals can be provided. Where the transcriptional termination signals are not satisfactorily functional in the expression host cell, then a 3'region functional in the host cell can be substituted.

Two DNA sequences (such as a promoter region sequence and an tpr1 or tpr2 sequence) are said to be operably linked if the nature of the linkage between the two DNA sequences does not (1) result in the introduction of a frame-shift mutation, (2) interfere with the ability of the promoter region sequence to direct the transcription of an tpr1 or tpr2 gene sequence, or (3) interfere with the ability of the tpr1 or tpr2 gene sequence to be transcribed by the promoter region sequence. Thus, a promoter region would be operably linked to a DNA sequence if the promoter were capable of effecting transcription of that DNA sequence.

The present invention encompasses the expression of the tpr1 or tpr2 gene (or a functional derivative thereof in either prokaryotic or eukaryotic cells. Prokaryotic hosts are, generally, the most efficient and convenient for the production of recombinant proteins and, therefore, are preferred for the expression of the tpr1 or tpr2 gene.

Prokaryotes most frequently are represented by various strains of *E. coli*. However, other microbial strains can also be used, including other bacterial strains. In prokaryotic systems, plasmid vectors that contain replication sites and control sequences derived from a species compatible with the host can be used. Examples of suitable plasmid vectors include pBR322, pUC118, pUC119 and the like; suitable phage or bacteriophage vectors include λgt10, λgt11 and the like; and suitable virus vectors include pMAM-neo, pKRC and the like. Preferably, the selected vector of the present invention has the capacity to replicate in the selected host cell.

Recognized prokaryotic hosts include bacteria such as *E. coli*, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

To express tpr1 or tpr2 in a prokaryotic cell, it is necessary to operably link the tpr1 or tpr2 sequence to a functional prokaryotic promoter. Such promoters can be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pBR325, and the like. Examples of inducible prokaryotic promoters include the major right and left promoters of bacteriophage, λ($P_L$ and $P_R$), the trp, recA, lacZ, lacI, and gal promoters of *E. coli*, the α-amylase (Ulmanen et al., *J. Bacteriol.* 162:176–182 (1985)) and the ζ-28-specific promoters of *B. subtilis* (Gilman et al., *Gene sequence* 32:11–20 (1984)), the promoters of the bacteriophages of Bacillus (Gryczan, In: *The Molecular Biology of the Bacilli*, Academic Press, Inc., NY (1982)), and Streptomyces promoters (Ward et al., *Mol. Gen. Genet.* 203:468–478 (1986)). Prokaryotic promoters are reviewed by Glick (*J. Ind. Microbiol.* 1:277–282 (1987)); Cenatiempo (*Biochimie* 68:505–516 (1986)); and Gottesman (*Ann. Rev. Genet.* 18:415–442 (1984)).

Proper expression in a prokaryotic cell also requires the presence of a ribosome binding site upstream of the gene sequence-encoding sequence. Such ribosome binding sites are disclosed, for example, by Gold et al. (*Ann. Rev. Microbiol.* 35:365–404 (1981)).

The selection of control sequences, expression vectors, transformation methods, and the like, are dependent on the type of host cell used to express the gene. As used herein, "cell", "cell line", and "cell culture" can be used interchangeably and all such designations include progeny. Thus, the words "transformants" or "transformed cells" include the primary subject cell and cultures derived therefrom, without regard to the number of transfers. It is also understood that all progeny can not be precisely identical in DNA content, due to deliberate or inadvertent mutations. However, as defined, mutant progeny have the same functionality as that of the originally transformed cell.

Host cells which can be used in the expression systems of the present invention are not strictly limited, provided that they are suitable for use in the expression of the tpr1 or tpr2 peptide of interest. Suitable hosts include eukaryotic cells.

Preferred eukaryotic hosts include, for example, yeast, fungi, insect cells, mammalian cells either in vivo, or in tissue culture. Preferred mammalian cells include HeLa cells, cells of fibroblast origin such as VERO or CHO-K1, or cells of lymphoid origin and their derivatives.

In addition, plant cells are also available as hosts, alid control sequences compatible with plant cells are available, such as the cauliflower mosaic virus 35S and 19S, and nopaline synthase promoter and polyadenylation signal sequences.

Another preferred host is an insect cell, for example Drosophila larvae. Using insect cells as hosts, the Drosophila alcohol dehydrogenase promoter can be used. Rubin, *Science* 240:1453–1459 (1988). Alternatively, baculovirus vectors can be engineered to express large amounts of tpr1 or tpr2 in insects cells (Jasny, *Science* 238:1653 (1987); Miller et al., In: *Genetic Engineering* (1986), Setlow, J. K., et al., eds., *Plenum*, Vol. 8, pp. 277–297).

Different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of the heterologous tpr1 or tpr2 protein. Furthermore, different vector/host expression systems can effect processing reactions such as proteolytic cleavages to different extents.

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals.

Yeast provides substantial advantages in that it can also carry out post-translational peptide modifications. A number of recombinant DNA strategies exist which utilize strong promoter sequences and high copy number of plasmids which can be utilized.for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of tpr1 or tpr2.

A wide variety of transcriptional and translational regulatory sequences can be employed, depending upon the nature of the host. The transcriptional and translational regulatory signals can be derived from viral sources, such as adenovirus, bovine papirnoma virus, simian virus, or the like, where the regulatory signals are associated with a particular gene sequence which has a high level of expression. Alternatively, promoters from mammalian expression products, such as actin, collagen, myosin, and the like, can be employed. Transcriptional initiation regulatory signals can be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

As discussed above, expression of tpr1 or tpr2 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288 (1982)); the TK promoter of Herpes virus (McKnight, *Cell* 31:355–365 (1982)); the SV40 early promoter (Benoist et al., *Nature* (London) 290:304–310 (1981)); the yeast gal4 gene sequence promoter (Johnston et al., *Proc. Natl. Acad. Sci. (USA)* 79:6971–6975 (1982), Silver et al., *Proc. Natl. Acad. Sci. (USA)* 81:5951–5955 (1984)).

As is widely known, translation of eukaryotic mRNA usually initiates at the first AUG codon encountered—but not always. Prediction of whether a particular methionine codon will be used for translation initiation is described by Kozak, *Nucl. Acids Res.* 15:8125–32 (1987). It is preferable to ensure that the linkage between a eukaryotic promoter and a DNA sequence which encodes tpr1 or tpr2 does not contain any intervening codons which are capable of encoding a methionine (i.e., ATG). The presence of such codons results either in a formation of a fusion protein (if the ATG codon is in the same reading frame as the tpr1 or tpr2 coding sequence) or a frame-shift mutation (if the ATG codon is not in the same reading frame as the tpr1 or tpr2 coding sequence).

A tpr1 or tpr2 nucleic acid molecule and an operably linked promoter can be introduced into a recipient prokaryotic or eukaryotic cell either as a nonreplicating DNA (or RNA) molecule, which can either be a linear molecule or, more preferably, a closed covalent circular molecule. Since such molecules are incapable of autonomous replication, the expression of the gene can occur through the transient expression of the introduced sequence. Alternatively, permanent expression can occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker can provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements can also be needed for optimal synthesis of single chain binding protein mRNA. These elements can include splice signals, as well as transcription promoters, enhancers, and termination signals. cDNA expression vectors incorporating such elements include those described by Okayama, *Molec. Cell. Biol.* 3:280 (1983).

In a preferred embodiment, the introduced nucleic acid molecule will be incorporated into a plasmid or viral vector capable of autonomous replication in the recipient host. Any of a wide variety of vectors can be employed for this purpose. Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, πVX. Such plasmids are, for example, disclosed by Sambrook (cf. *Molecular Cloning: A Laboratory Manual*, second edition, edited by Sambrook, Fritsch, & Maniatis, Cold Spring Harbor Laboratory, 1989). Bacillus plasmids include pC194, pC221, pT127, and the like. Such plasmids are disclosed by Gryczan(In: *The Molecular Biology of the Bacilli*, Academic Press, New York (1982), pp. 307–329). Suitable Streptomyces plasmids include pIJ101 (Kendall et al., *J. Bacteriol.* 169:4177–4183 (1987)), and streptomyces bacteriophages such as φC31 (Chater et al., In: *Sixth International Symposium on Actinomycetales Biology*, Akademiai Kaido, Budapest, Hungary (1986), pp.45–54). Pseudomonas plasmids are reviewed by John et al. (*Rev. Infect. Dis.* 8:693–704 (1986)), and Izaki (*Jpn. J. Bacteriol* 33:729–742 (1978)).

Preferred eukaryotic plasmids include, for example, BPV, vaccinia, SV40, 2-micron circle, and the like, or their derivatives. Such plasmids are well known in the art (Botstein et al., *Miami Wntr. Symp.* 19:265–274 (1982); Broach, In: *The Molecular Biology of the Yeast Saccharomyces: Life Cycle and Inheritance*, Cold Spring Harbor Laboratory, Cold Spring Harbor, N.Y., p. 445–470 (1981); Broach, *Cell* 28:203–204 (1982); Bollon et al., *J. Clin. Hematol. Oncol.* 10:39–48 (1980); Maniatis, In: *Cell Biology: A Comprehensive Treatise*, Vol. 3, Gene Sequence Expression, Academic Press, New York, pp. 563–608 (1980)).

Once the vector or nucleic acid molecule containing the construct(s) has been prepared for expression, the DNA construct(s) can be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells.

Expression of the cloned gene molecule(s) results in the production of tpr1 or tpr2. This can take place in the transformed cells as such, or following the induction of these cells to differentiate (for example, by administration of bromodeoxyuracil to neuroblastoma cells or the like).

VIII. An Antibody Having Binding Affinity to an tpr1 or tpr2 Polypeptide and a Hybridoma Containing the Antibody In another embodiment, the present invention relates to an antibody having binding affinity specifically to an tpr1 or tpr2 polypeptide as described above or specifically to a tpr1 or tpr2 polypeptide binding fragment thereof. An antibody binds specifically to a tpr1 or tpr2 polpeptide or binding fragment thereof if it does not bind to a TPR polypeptide known in the prior art. Those which bind selectively to tpr1 or tpr2 would be chosen for use in methods which could include, but should not be limited to, the analysis of altered tpr1 or tpr2 expression in tissue containing tpr1 or tpr2.

The tpr1 or tpr2 proteins of the present invention can be used in a variety of procedures and methods, such as for the generation of antibodies, for use in identifying pharmaceutical compositions, and for studying DNA/protein interaction.

The tpr1 or tpr2 peptide of the present invention can be used to produce antibodies or hybridomas. One skilled in the art will recognize that if an antibody is desired, such a peptide would be generated as described herein and used as an immunogen.

The antibodies of the present invention include monoclonal and polyclonal antibodies, as well as fragments of these antibodies. The invention further includes single chain antibodies. Antibody fragments which contain the idiotype of the molecule can be generated by known techniques. For example, such fragments include but are not limited to: the F(ab')$_2$ fragment; the Fab' fragments, Fab fragments, and Fv fragments.

Of special interest to the present invention are antibodies to tpr1 or tpr2 which are produced in humans, or are "humanized" (i.e. non-immunogenic in a human) by recombinant or other technology. Humanized antibodies can be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 240:1041–1043 (1988); Liu, A. Y. et al., *Proc. Natl. Acad. Sci. USA* 84:3439–3443 (1987); Liu, A. Y. et al., *J. Immunol.* 139:3521–3526 (1987); Sun, L. K. et al., *Proc. Natl. Acad. Sci. USA* 84:214–218 (1987); Nishimura, Y. et al., *Canc. Res.* 47:999–1005 (1987); Wood, C. R. et al., *Nature* 314:446–449 (1985)); Shaw et al., *J. Natl.Cancer Inst.* 80:1553–1559 (1988). General reviews of "humanized" chimeric antibodies are provided by Morrison, S. L. (*Science*, 229:1202–1207 (1985)) and by Oi, V. T. et al., *BioTechniques* 4:214 (1986)). Suitable "humanized" antibodies can be alternatively produced by CDR or CEA substitution (Jones, P. T. et al., *Nature* 321:552–525 (1986); Verhoeyan et al., *Science* 239:1534 (1988); Beidler, C. B. et al., *J. Immunol.* 141:4053–4060 (1988)).

In another embodiment, the present invention relates to a hybridoma which produces the above-described monoclonal antibody. A hybridoma is an immortalized cell line which is capable of secreting a specific monoclonal antibody.

In general, techniques for preparing monoclopal antibodies and hybridomas are well known in the art (Campbell, "*Monoclonal Antibody Technology: Laboratory Techniques in Biochemistry and Molecular Biology,*" Elsevier Science Publishers, Amsterdam, The Netherlands (1984); St. Groth et al., *J. Immunol. Methods* 35:1–21 (1980)).

Any animal (mouse, rabbit, and the like) which is known to produce antibodies can be immunized with the selected polypeptide. Methods for immunization are well known in the art. Such methods include subcutaneous or interiperitoneal injection of the polypeptide. One skilled in the art will recognize that the amount of polypeptide used for immunization will vary based on the animal which is immunized, the antigenicity of the polypeptide and the site of injection.

The polypeptide can be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)).

Hybridomas secreting the desired antibodies are cloned and the class and subclass is determined using procedures known in the art (Campbell, *Monoclonal Antibody Technology: Laboratory Techniques in Biochemistry and Molecular Biology*, supra (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Stemberger et al., *J. Histochem. Cytochem.* 18:315 (1970); Bayer et al., *Meth. Enzym.* 62:308 (1979); Engval et al., *Immunol.* 109:129 (1972); Goding, *J. Immunol. Meth.* 13:215 (1976)). The labeled antibodies of the present invention can be used for in vitro, in vivo, and in situ assays to identify cells or tissues which express a specific peptide.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "*Handbook of Experimental Immunology*" 4th Ed., Blackwell Scientific Publications, Oxford, England, Chapter 10 (1986); Jacoby et al., *Meth. Enzym.* 34 Academic Press, New York (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al, "Application of Synthetic Peptides: Antisense Peptides", *In Synthetic Peptides, A User's Guide*, W. H. Freeman, N.Y., pp. 289–307 (1992), and Kaspezak et al., *Biochemistry* 28:9230–8 (1989).

Anti-peptide peptides can be generated in one of two fashions. First, the anti-peptide peptides can be generated by replacing the basic amino acid residues found in the tpr1 or tpr2 peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

IX. A Method of Detecting an tpr1 or tpr2 Polypeptide in a Sample

In another embodiment, the present invention relates to a method of detecting a tpr1 or tpr2 polypeptide in a sample, comprising: a) contacting the sample with an above-described antibody, under conditions such that immunocomplexes form, and b) detecting the presence of the antibody bound to the polypeptide. In detail, the methods comprise incubating a test sample with one or more of the antibodies of the present invention and assaying whether the antibody binds to the test sample. Altered levels of tpr1 or tpr2 in a sample as compared to normal levels can indicate a specific disease.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, difflusion based Ouchterlony, or rocket immunofluorescent assays) can readily be adapted to employ the antibodies of the present invention. Examples of such assays can be found in Chard, *An Introduction to Radioimmunoassay and Related Techniques*, Elsevier Science Publishers, Amsterdam, The Netherlands (1986); Bullock et al., *Techniques in Immunocytochemistry*, Academic Press, Orlando, Fla. Vol. 1 (1982), Vol. 2 (1983), Vol. 3 (1985); Tijssen, *Practice and Theory of Enzyme Immunoassays: Laboratory Techniques in Biochemistry and Molecular Biology*, Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

X. A Diagnostic Kit Comprising Antibodies to tpr1 or tpr2 Polypeptide

In another embodiment of the present invention, a kit is provided which contains all the necessary reagents to carry out the previously described methods of detection. The kit can comprise: i) a first container means containing an above-described antibody, and ii) second container means containing a conjugate comprising a binding partner of the antibody and a label. In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit can be as described above for nucleic acid probe kits.

One skilled in the art will readily recognize that the antibodies described in the present invention can readily be incorporated into one of the established kit formats which are well known in the art.

XI. Diagnostic Screening and Treatment

It is to be understood that although the following discussion is specifically directed to human patients, the teachings are also applicable to any animal that expresses tpr1 or tpr2.

The diagnostic and screening methods of the invention are especially usefll for a patient suspected of being at risk for developing a disease associated with an altered expression level of tpr1 or tpr2 based on family history, or a patient in which it is desired to diagnose a tpr1 or tpr2-related disease.

According to the invention, presymptomatic screening of an individual in need of such screening is now possible using DNA encoding the tpr1 or tpr2 protein of the invention. The screening method of the invention allows a presymptomatic diagnosis, including prenatal diagnosis, of the presence of a missing or aberrant tpr1 or tpr2 gene in individuals, and thus an opinion concerning the likelihood that such individual would develop or has developed a tpr1 or tpr2-associated disease. This is especially valuable for the identification of carriers of altered or missing tpr1 or tpr2 genes, for example, from individuals with a family history of a tpr1 or tpr2-associated disease. Early diagnosis is also desired to maximize appropriate timely intervention.

In one preferred embodiment of the method of screening, a tissue sample would be taken from such individual, and screened for (1) the presence of the "normal" tpr1 or tpr2 gene; (2) the presence of tpr1 or tpr2 mRNA and/or (3) the presence of tpr1 or tpr2 protein. The normal human gene can be characterized based upon, for example, detection of restriction digestion patterns in "normal" versus the patient's DNA, including RFLP analysis, using DNA probes prepared against the tpr1 or tpr2 sequence (or a functional fragment thereof) taught in the invention. Similarly, tpr1 or tpr2 mRNA can be characterized and compared to normal tpr1 or tpr2 mRNA (a) levels and/or (b) size as found in a human population not at risk of developing tpr1 or tpr2-associated disease using similar probes. Lastly, tpr1 or tpr2 protein can be (a) detected and/or (b) quantitated using a biological assay for tpr1 or tpr2 activity or using anjinmunological assay and tpr1 or tpr2 antibodies. When assaying tpr1 or tpr2 protein, the immunological assay is preferred for its speed. An (1) aberrant tpr1 or tpr2 DNA size pattern, and/or (2) aberrant tpr1 or tpr2 mRNA sizes or levels and/or (3) aberrant tpr1 or tpr2 protein levels would indicate that the patient is at risk for developing a tpr1 or tpr2-associated disease.

The screening and diagnostic methods of the invention do not require that the entire tpr1 or tpr2 DNA coding sequence be used for the probe. Rather, it is only necessary to use a fragment or length of nucleic acid that is sufficient to detect the presence of the tpr1 or tpr2 gene in a DNA preparation from a normal or affected individual, the absence of such gene, or an altered physical property of such gene (such as a change in electrophoretic migration pattern).

Prenatal diagnosis can be performed when desired, using any known method to obtain fetal cells, including amniocentesis, chorionic villous sampling (CVS), and fetoscopy. Prenatal chromosome analysis can be used to determine if the portion of the chromosome possessing the normal tpr1 or tpr2 gene is present in a heterozygous state.

In the method of treating a tpr1 or tpr2-associated disease in a patient in need of such treatment, functional tpr1 or tpr2 DNA can be provided to the cells of such patient in a manner and amount that permits the expression of the tpr1 or tpr2 protein provided by such gene, for a time and in a quantity sufficient to treat such patient. Many vector systems are known in the art to provide such delivery to human patients in need of a gene or protein missing from the cell. For example, retrovirus systems can be used, especially modified retrovirus systems and especially herpes simplex virus systems. Such methods are provided for, in, for example, the teachings of Breakefield, X. A. et al., *The New Biologist* 3:203–218 (1991); Huang, Q. et al., *Experimental Neurology* 115:303–316 (1992), WO93/03743 and WO90/09441. Delivery of a DNA sequence encoding a functional tpr1 or tpr2 protein will effectively replace the missing or mutated tpr1 or tpr2 gene of the invention.

In another embodiment, the present invention relates to a method of administering tpr1 or tpr2 to an animal (preferably, a mammal (specifically, a human)) in an amount sufficient to effect an altered level of tpr1 or tpr2 in the animal. The administered tpr1 or tpr2 could specifically effect tpr1 or tpr2 associated functions.

One skilled in the art will appreciate that the amounts to be administered for any particular treatment protocol can readily be determined. The dosage should not be so large as to cause adverse side effects, such as unwanted crossreactions, anaphylactic reactions, and the like. Generally, the dosage will vary with the age, condition, sex and extent of disease in the patient, counter indications, if any, and other such variables, to be adjusted by the individual physician. Dosage can vary from 0.001 mg/kg to 50 mg/kg of tpr1 or tpr2, in one or more administrations daily, for one or several days. Tpr1 or tpr2 can be administered parenterally by injection or by gradual perfusion over time. It can be administered intravenously, intraperitoneally, intramuscularly, or subcutaneously.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present, such as, for example, antimicrobials, antioxidants, chelating agents, inert gases and the like. See, generally, *Remington's Pharmaceutical Science*, 16th Ed., Mack Eds. (1980).

In another embodiment, the present invention relates to a pharmaceutical composition comprising tpr1 or tpr2 in an amount sufficient to alter tpr1 or tpr2 associated activity, and a pharmaceutically acceptable diluent, carrier, or excipient. Appropriate concentrations and dosage unit sizes can be readily determined by one skilled in the art as described above (See, for example, *Remington's Pharmaceutical Sciences* (16th ed., Osol, A., Ed., Mack, Easton Pa. (1980) and WO 91/19008).

XII. Transgenic tpr1 or tpr2 "Knock-Out" Mice
Methods of Generating Transgenic Non-Human Animals The non-human animals of the invention comprise any animal having a transgenic interruption or alteration of the endogenous tpr1 or tpr2 gene(s) (knock-out animals) and/or into the genome of which has been introduced one or more transgenes that direct the expression of human tpr1 or tpr2.

Such non-human animals include vertebrates such as rodents, non-human primates, sheep, dog, cow, amphibians, reptiles, etc. Preferred non-human animals are selected from non-human mammalian species of animals, most preferably, animals from the rodent family including rats and mice, most preferably mice.

The transgenic animals of the invention are animals into which has been introduced by nonnatural means (i.e., by human manipulation), one or more genes that do not occur naturally in the animal, e.g., foreign genes, genetically engineered endogenous genes, etc. The nonnaturally introduced genes, known as transgenes, may be from the same or a different species as the animal but not naturally found in the animal in the configuration and/or at the chromosomal locus conferred by the transgene. Transgenes may comprise foreign DNA sequences, i.e., sequences not normally found in the genome of the host animal. Alternatively or additionally, transgenes may comprise endogenous DNA sequences that are abnormal in that they have been rearranged or mutated in vitro in order to alter the normal in vivo pattern of expression of the gene, or to alter or eliminate the biological activity of an endogenous gene product encoded by the gene. (Watson, J. D., et al., in *Recombinant DNA*, 2d Ed., W.H. Freeman & Co., New York (1992), pages 255–272; Gordon, J. W., *Intl. Rev. Cytol.* 115:171–229 (1989); Jaenisch, R., *Science* 240:1468–1474 (1989); Rossant, J., *Neuron* 2:323–334 (1990)).

The transgenic non-human animals of the invention are produced by introducing transgenes into the germline of the non-human animal. Embryonic target cells at various developmental stages are used to introduce the transgenes of the invention. Different methods are used depending on the stage of development of the embryonic target cell(s).

1. Microinjection of zygotes is a preferred method for incorporating transgenes into animal genomes in the course of practicing the invention. A zygote, a fertilized ovum that has not undergone pronuclei fusion or subsequent cell division, is the preferred target cell for microinjection of transgenic DNA sequences. The murine male pronucleus reaches a size of approximately 20 micrometers in diameter, a feature which allows for the reproducible injection of 1-2 picoliters of a solution containing transgenic DNA sequences. The use of a zygote for introduction of transgenes has the advantage that, in most cases, the injected transgenic DNA sequences will be incorporated into the host animal's genome before the first cell division (Brinster, et al., *Proc. Natl. Acad. Sci.* (USA) 82:4438–4442 (1985)). As a consequence, all cells of the resultant transgenic animals (founder animals) stably carry an incorporated transgene at a particular genetic locus, referred to as a transgenic allele. The transgenic allele demonstrates Mendelian inheritance: half of the offspring resulting from the cross of a transgenic animal with a non-transgenic animal will inherit the transgenic allele, in accordance with Mendel's rules of random assortment.

2. Viral integration can also be used to introduce the transgenes of the invention into an animal. The developing embryos are cultured in vitro to the developmental stage known as a blastocyst. At this time, the,blastomeres may be infected with appropriate retroviruses (Jaenich, R., *Proc. Natl. Sci.* (USA) 73:1260–1264 (1976)). Infection of the blastomeres is enhanced by enzymatic removal of the zona pellucida (Hogan, et al., in *Manipulating the Mouse Embryo*, Cold Spring Harbor Press, Cold Spring Harbor, N.Y. (1986)). Transgenes are introduced via viral vectors which are typically replication-defective but which remain competent for integration of viral-associated DNA sequences, including transgenic DNA sequences linked to such viral sequences, into the host animal's genome (Jahner, et al., *Proc. Natl. Acad. Sci.* (USA) 82:6927–6931 (1985); Van der Putten, et al., *Proc. Natl. Acad. Sci.* (USA) 82:6148–6152 (1985)). Transfection is easily and efficiently obtained by culture of blastomeres on a mono-layer of cells producing the transgene-containing viral vector (Van der Putten, et al., *Proc. Natl. Acad. Sci.* (USA) 82:6148–6152 (1985); Stewart, et al., *EMBO Journal* 6:383–388 (1987)). Alternatively, infection may be performed at a later stage, such as a blastocoele (Jahner, D., et al., *Nature* 298:623–628 (1982)). In any event, most transgenic founder animals produced by viral integration will be mosaics for the transgenic allele; that is, the transgene is incorporated into only a subset of all the cells that form the transgenic founder animal. Moreover, multiple viral integration events may occur in a single founder animal, generating multiple transgenic alleles which will segregate in future generations of offspring. Introduction of transgenes into germline cells by this method is possible but probably occurs at a low frequency (Jahner, D., et al., *Nature* 298:623–628 (1982)). However, once a transgene has been introduced into germline cells by this method, offspring may be produced in which the transgenic allele is present in all of the animal's cells, i.e., in both somatic and germline cells.

3. Embryonic stem (ES) cells can also serve as target cells for introduction of the transgenes of the invention into animals. ES cells are obtained from pre-implantation embryos that are cultured in vitro (Evans, M. J., et al., *Nature* 292:154–156 (1981); Bradley, M. O., et al., *Nature* 309:255–258 (1984); Gossler, et al., *Proc. Natl. Acad. Sci.* (USA) 83:9065–9069 (1986); Robertson et al., *Nature* 322:445–448 (1986); Robertson, E. J., in *Teratocarcinomas and Embryonic Stem Cells: A Practical Approach*, Robertson, E. J., ed., IRL Press, Oxford (1987), pages 71–112). ES cells, which are commercially available (from, e.g., Genome Systems, Inc., St. Louis, Mo.), can be transformed with one or more transgenes by established methods (Lovell-Badge, R. H., in *Teratocarcinomas and Embryonic Stem Cells: A Practical Approach*, Robertson, E. J., ed., IRL Press, Oxford (1987), pages 153–182). Transformed ES cells can be combined with an animal blastocyst, whereafter the ES cells colonize the embryo and contribute to the germline of the resulting animal, which is a chimera (composed of cells derived from two or more animals) (Jaenisch, R, *Science* 240:1468–1474 (1988); Bradley, A., in *Teratocarcinomas and Embryonic Stem Cells: A Practical Approach*, Robertson, E. J., ed., IRL Press, Oxford (1987), pages 113–151). Again, once a transgene has been introduced into germline cells by this method, offspring may be produced in which the transgenic allele is present in all of the animal's cells, i.e., in both somatic and germline cells.

However it occurs, the initial introduction of a transgene is a Lamarckian (non-Mendelian) event. However, the transgenes of the invention may be stably integrated into germ line cells and transmitted to offspring of the transgenic animal as Mendelian loci. Other transgenic techniques result in mosaic transgenic animals, in which some cells carry the transgenes and other cells do not. In mosaic transgenic animals in which germ line cells do not carry the transgenes, transmission of the transgenes to offspring does not occur. Nevertheless, mosaic transgenic animals are capable of demonstrating phenotypes associated with the transgenes.

Transgenes may be introduced into non-human animals in order to provide animal models for human diseases. Transgenes that result in such animal models include, e.g., transgenes that encode mutant gene products associated with an inborn error of metabolism in a human genetic disease and transgenes that encode a human factor required to confer susceptibility to a human pathogen (i.e., a bacterium, virus, or other pathogenic microorganism) (Leder et al., U.S. Pat. No. 5,175,383 (Dec. 29, 1992); Kindt et al., U.S. Pat. No. 5,183,949 (Feb. 2, 1993); Small et al., *Cell* 46:13–18 (1986); Hooper et al., *Nature*, 326:292–295 (1987); Stacey et al., *Nature* 332:131–136 (1988); Windle et al., *Nature* 343:665–669 (1990); Katz et al., *Cell* 74:1089–1100 (1993)). Transgenically introduced mutations comprise null ("knock-out") alleles in which a DNA sequence encoding a selectable and/or detectable marker is substituted for a genetic sequence normally endogenous to a non-human animal. Resultant transgenic non-human animals that are predisposed to a disease, or in which the transgene causes a disease, may be used to identify compositions that induce the disease and to evaluate the pathogenic potential of compositions known or suspected to induce the disease (Bems, A. J. M., U.S. Pat. No. 5,174,986 (Dec. 29, 1992)), or to evaluate compositions which may be used to treat the disease or ameliorate the symptoms thereof (Scott et al., WO 94/12627 (1994)).

Offspring that have inherited the transgenes of the invention are distinguished from littermates that have not inherited transgenes by analysis of genetic material from the offspring for the presence of biomolecules that comprise unique sequences corresponding to sequences of, or encoded by, the transgenes of the invention. For example, biological fluids that contain polypeptides uniquely encoded by the selectable marker of the transgenes of the invention may be immunoassayed for the presence of the polypeptides. A more simple and reliable means of identing transgenic offspring comprises obtaining a tissue sample from an extremity of an animal, e.g., a tail, and analyzing the sample for the presence of nucleic acid sequences-corresponding to the DNA sequence of a unique portion or portions of the transgenes of the invention, such as the selectable marker thereof. The presence of such nucleic acid sequences may be determined by, e.g., hybridization ("Southern") analysis with DNA sequences corresponding to unique portions of the transgene, analysis of the products of PCR reactions using DNA sequences in a sample as substrates and oligonucleotides derived from the transgene's DNA sequence, etc.

The present invention is described in furter detail in the following nonlimiting examples.

EXAMPLES

The following protocols and experimental details are referenced in the examples that follow.

Interaction Trap

A detailed description of the methods and plasmids used herein is provided in Gyuris, J. et al., *Cell* 75:791–803 (1993), and in Zervos, A. S., *Cell* 72:223–232 (1993). The bait, LexA-NF1a, was constructed by PCR amplifying a fragment of the NF1 coding sequence (GenBank #M89914) (Bemards, A. et al., *DNA Cell Biol.* 11:727–734 (1992)) extending from bases 3705–4862 (codons 1170–1555) using primers containing a SalI restriction enzyme site (primer 3A: 5'GGG<u>GTCGAC</u>ACAAGGATCTCCAGACAAG 3' (SEQ ID NO:5); primer 3B: 5'GGG<u>GTCGAC</u>TTATGCCACAGGTTTGTGC TCTGGAGG 3') (SEQ ID NO:6) and subcloning the SalI (underlined) digested fragment into the SalI site of LexA(1-202)+PL (Gyuris, J. et al., *Cell* 75:791–803 (1993); Zervos, A. S., *Cell* 72:223–232 (1993)). Sequence analysis revealed a single base pair deletion of position 4514, which is predicted to result in a two codon sequence change at codons 1440 and 1441 (GenBank #P21359): Lys, Leu to Leu, Ser followed by a termination codon.

To identify proteins potentially interacting with this region of neurofibromin, yeast strain, EGY48, containing the LexAop-LEU2 and lacZ reporters and the LexA-NF1 bait plasmid was transformed (Schiestl & Gietz, *Curr. Genet.* 16:339–346 (1989)) with the HeLa cell interaction library described in (Gyuris, J. et al., *Cell* 75:791–803 (1993); Zervos, A. S., *Cell* 72:223–232 (1993)). In this library, cDNAs are conditionally expressed from a galactose inducible promoter as fusion proteins with an *E. coli* derived activation domain. $2 \times 10^6$ primary transformants were recovered, harvested, and suspended in one pellet volume of 65% glycerol, 10 mM Tris-HCl (pH 7.5), 10 mM $MgCl_2$, and frozen in aliquots. After determining the plating efficiency, approximately $2 \times 10^7$ colony forming units were plated on Ura⁻, His⁻, Trp⁻, Leu⁻ plates after galactose induction and 14 colonies were collected for analysis.

Probes and Blot Analysis

The tpr1 and tpr2 fragments used as probes are shown in FIG. 1. The tpr1 A and B probes were isolated as 81 bp EcoRI, and 1.2 kb EcoRI/XhoI fragments and include nucleotides 257 to 311, and 312 to 1407 of the full length tpr1 cDNA (FIG. 1), respectively. The tpr2 probe was isolated from the interaction trap library clone tpr2a as an EcoRI/XhoI fragment and includes nucleotides 1 to 1068 of the full length tpr2 cDNA. All probes were radioactively labeled by the random primer method (Feinberg & Vogelstein, *Anal. Biochem.* 132:6–13 (1983)). For Southern analysis, DNA was digested with restriction enzymes, electrophoresed in 1% agarose gels transferred to Hybond membrane and hybridized by standard methods (Sambrook, J. et al., eds., *Molecular Cloning: A Laboratoiy Manual*, Cold Spring Harbor Laboratory Press, Cold Spring Harbor, N.Y. (1989)). For Northern analysis, a commercially obtained blot (Clonetech) was hybridized as described (Bernards & delaMonte, *EMBO. J.* 9:2279–2287 (1990)).

PCR Mapping of tpr1

Figure 4A:
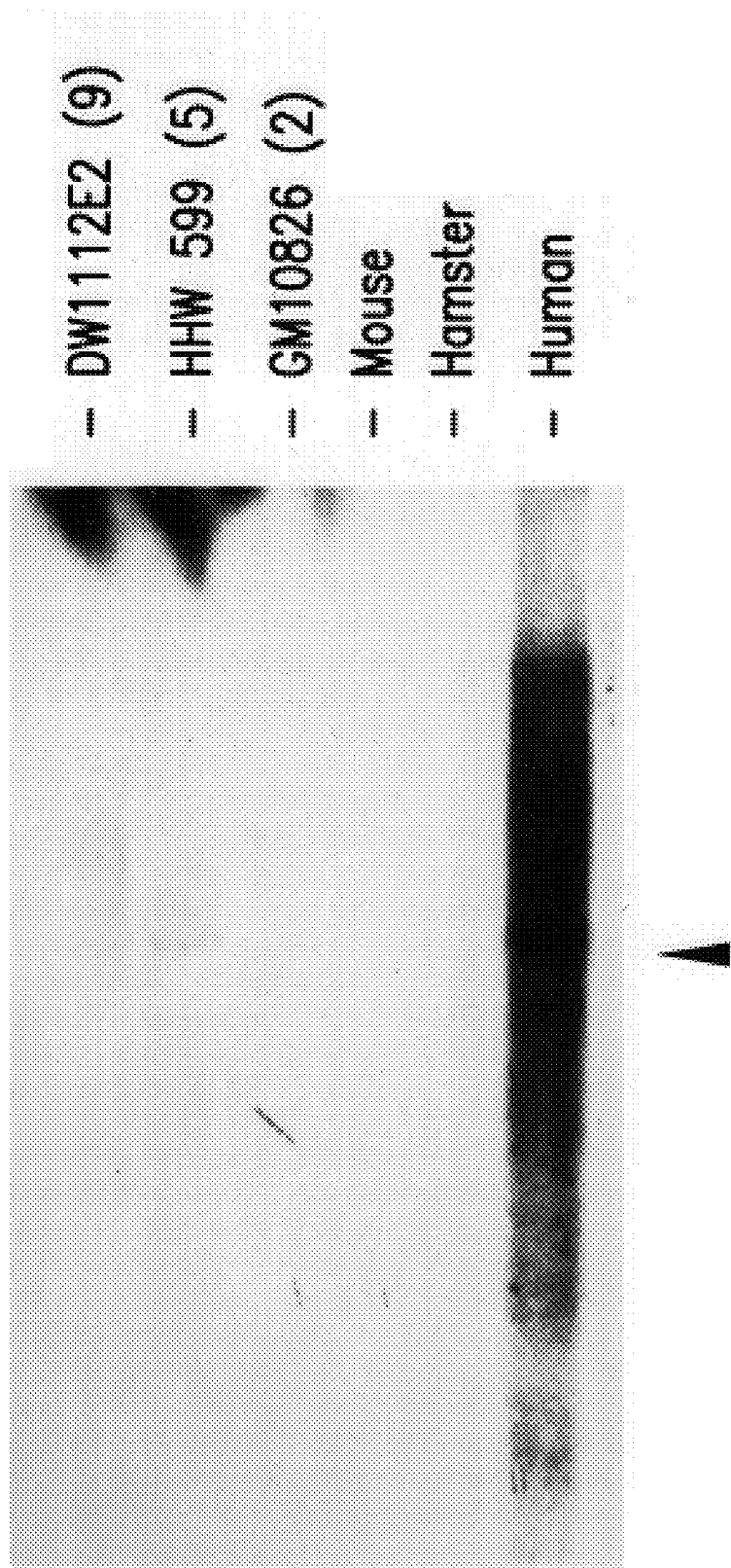
FIGS. 4A–B Chromosomal localization of tpr1.
Figure 4B:

Based on the sequence of the 3' untranslated region of tpr1, two synthetic oligonucleotide primers tprb (5'CTTGGGAACTTGGTTCTCCG3', position 810-829 of FIG. 2) (SEQ ID NO:7) and tpr1c (5'CATGTCTGGGCAGTCTCCCAAC3', position 1278-1299 of FIG. 2) (SEQ ID NO:8) encompassing a 488 bp fragment were synthesized. These primers were used to amplify genomic DNA from a chromosome 5 deletion panel (FIG. 4B). Genomic DNA was amplified in a thermal cycler by the following procedure: 94° C. for 5 min. followed by 35 cycles of (94° C. denaturation for 1 min, 60° C. annealing for 1 min., and 72° C. for 2 min.).

Library Screening cDNA clones were isolated from the following cDNA libraries: tpr1, human fetal liver in λgt10 (Clonetech) and human brain in λZAP (Stratagene) and tpr2, human heart and human fetal retina in λZAP (Stratagene) by standard techniques (Sambrook, J. et al., eds., *Molecular Cloning: A Laboratory Manual*, Cold Spring Harbor Laboratory Press, Cold Spring Harbor, N.Y. (1989)). Hybridization conditions were 65° C. in 6×SSC, 1×Denhardt's solution, 0.5% SDS.

Phage clones of interest were plaque purified, and cDNA inserts were subcloned into plasmid vectors.

Sequence Analysis

All sequences shown were determined on both DNA strands or at least twice on the same strand. Sequences were analyzed using software provided by the Genetics Computer Group (GCG) (Devereaux, J. et al., Nucleic Acids. Res. 12:387–395 (1984)) and the BLAST network service at the National Center for Biotechnology Information (Altschul, S.C. et al., J. Mol. Biol. 215:403–410 (1990); Gish & States, Nature Genetics 3:266–272 (1993)).

Example 1

Interaction Trap Screen

The interaction trap system (Gyuris, J. et al., Cell 75:791–803 (1993)) was used to identify proteins that interact with a 271 amino acid "bait" representing a truncated form of the neurofibromin GAP-related domain (GRD), terminated prematurely due to a one base pair deletion in codon 1439. A yeast reporter strain containing the pLexA-NF bait was transformed with a library of HeLa cell cDNAs expressed as fusions with an acidic activation domain. Fourteen colonies that grew only in the presence of galactose were identified. Of these, 2 (tpr1 and tpr2a) clearly showed galactose dependent blue color on X-gal medium and thus were selected for characterization (FIG. 1).

To determine whether any of the remaining 12 colonies contained cDNAs related to those in colonies 1 and/or 2, slot blots were performed on crude yeast DNA lysates. A third colony containing a larger, overlapping segment of the tpr2 cDNA, tpr2b, was identified (FIG. 1). The specificity of the interaction was tested by testing the ability of tpr1 to interact with a panel of unrelated baits, LexA-cdc2, LexA-Fus3, and LexA-bicoid (Zervos, A. S., Cell 72:223–232 (1993)) and with an analogous non-truncated neurofibromnin bait containing the GRD domain (codons 1170–1555) (Bemards, A. et al., DNA Cell Biol. 11:727–734 (1992)). Interaction was observed only with pLexA-NF and not with the intact NF1-GRD or with the unrelated baits, suggesting that tpr1 and tpr2 do not interact with normal neurofibromin in vivo, but interact specifically with the truncated version of the GRD represented by pLexA-NF.

Example 2

Sequence Analysis of tpr1

The tpr1, tpr2a, and tpr2b fusion clones were sequenced to identify the open reading frame in phase with the invariant amino-terminal activation domain of the vector. The structures of these cDNA clones are illustrated schematically in FIG. 1.

The tpr1 insert is a 1151 bp polyadenylated cDNA.containing a 669 bp open reading frame (ORF) and a 481 bp 3' untranslated region. A putative polyadenylation signal, AATAAAA is located 461 hp downstream of the stop codon and 21 bp upstream of the polyA tail. To determine the sequence of the fall length cDNA, human fetal liver and brain libraries were screened with the probe tpr1A (FIG. 1).

The human fetal brain library was made essentially by the procedure of Gyrus et al., Cell 75:791–803 (1993). Total RNA from ~1 gram of 22-week old human fetal frontal cortex was isolated. This tissue was composed of both neurons and neuroglia, as well as contaminating cells from the blood vessels. Total RNA was made by the guanidium isothiocyanate procedure. ~30 μg poly (A)$^+$mRNA was selected on an oligo(dT) cellulose column. 7 μg of the mRNA was used to make unidirectional cDNA with an EcoRI sticky end at the 5'-end and an XhoI sticky end at the 3'-end using a method similar to the variation of Gubler et al., Gene 25:263–269 (1983) described by Huse et al., Stratagene Strategies 1:1–3 (1988). The first strand was synthesized with Superscript (BRL) using a 50-mer primer (SEQ ID NO.:9):

5'-GAGAGAGAGAGAGAGAGAGAACTAGTCTCGAG TTTTTTTTTTTTTTTTTT-3'

This primer contains an 18 nt polydT tract, an XhoI site, and a 25 nt sequence to protect the XhoI site. The first-strand synthesis contained 5 me-dCTP instead of dCTP to protect internal XhoI sites from subsequent XhoI digestion. For the second strand synthesis, the mRNA/cDNA hybrid was treated with RNase H and E. coli DNA polymerase I. The resulting ends were made blunt by treatment with Klenow, mung bean nuclease, and then Klenow again. EcoRI adaptors were ligated onto them. The sequence of the adaptors is shown below:

5' AATTCGGCACGAGGCG 3' (SEQ ID NO.:10)
3' GCCGTGCTCCGC 5' (SEQ ID NO.:11)

All of the cDNA resulting from this synthesis was digested with XhoI and size fractionated on a 5–20% KoAc gradient. The fractions-representing cDNA larger than 1 kb was collected and the cDNA was precipitated and ligated into pJG4-5 (ampr, TRP1+, yeast 2 μm replictor) that had been cut downstream of the GAL1 promoter, an ATG, and sequences encoding the SV40 nuclear localization signal, a hemagglutinin epitope tag, and the B42 transcription activating domain.

3.5×10$^6$ primary transformants were collected, pooled, and grown in 8 liters of LB Amp to saturation. From these cells, ~8 mg plasmid DNA was isolated.

FIG. 2 shows a composite sequence derived from the two clones (ptpr2a and ptpr2b) isolated from these libraries and the tpr1 clone (ptpr1). ptpr1, ptpr2a, and ptpr2b were deposited on May 3, 1996 under the terms of the Budapest Treaty at the American Type Culture Collection (ATCC), 12301 Parklawn Dr., Rockville, Md. 20852 and given ATCC designations, 97530, 97531, and 97532, respectively.

A single G-to-C base difference at bp 167 was observed between the clone derived from the liver and brain library. This difference may either be due to an error introduced during reverse transcription or to a polymorphism. The full length cDNA is 1407 bp and contains 256 bp of 5' sequence that was not present in the tpr1 interacting cDNA (marked by an arrow in the Figure). The ORF contains a potential translation initiation site (ATG) (Kozak, M., Nucl. Acids. Res. 15:8125–8132 (1987)), with an in frame stop codon (TGA) 36 bp upstream. A BLASTN search of the NCBI databases identified 2 expressed sequence tags (F11544 and H00480) that extend the 5' end of tpr1 by 24 and 5 bases, respectively. The predicted 292 aa protein is quite hydrophilic as estimated from a Kyte-Doolittle hydropathy plot byte & Doolittle, J. Mol. Biol. 157:105–132 (1982)) and examination of the primary sequence reveals it to be rich in Glu residues, particularly in the N terminal half of the protein. No signal sequence, nuclear localization sequence (Dingwall & Laskey, Trends. Biochem. Sci. 16:47881 (1991)), or potential membrane spanning regions are apparent.

A search of the NCBI databases using BLAST to identify proteins with similarity to tpr1 revealed a significant region of resemblance in the predicted frame to the C. elegans F30H5 gene product (~32% identity) (Wilson, R. et al., *Nature* 368:32–38 (1994)), to the yeast heat shock protein, STI1 (~35% identity) (Nicolet & Craig, *Mol. Cell. Biol.* 9:3638–3646 (1989)) and to its human homologue IEF SSP 3521 (~35% identity) (Honore, B. et al., *J. Biol. Chem.* 267:8485–8491 (1992)), to the mouse extendin gene product (~33% identity) (Blatch, G. L. et al., *Proc. Am. Assoc. Cancer Res.* 36:68 (1995)), to the bovine PKR inhibitor (34% identity) (Lee, T. G. et al., *Mol. Cell. Biol.* 14:2331–2342 (1994)), and to several other members of the TPR family. Analysis of these sequence similarities revealed that they are confined to the TPR-containing regions of these proteins, except in the case of IEF SSP 3521, which also contains a local concentration of Glu residues and a short proline rich cluster near its N terminus. Outside of its 3 TPR units, this cDNA does not share sequence similarity with any other known genes or proteins.

Example 3

Sequence Analysis of tpr2

The tpr2 a and b library plasmids (FIG. 1) contain 1105 and 1650 bp partial cDNAs that share an 890 bp overlapping sequence. The tpr2a cDNA clone extends from position 1 at the 5' end of the sequence and appears to have been primed from an A rich region within the coding sequence of the tpr2 gene (bp 1069, GenBank U46571). The tpr2b clone extends from nt 234 to the polyA tail. A potential translation start site in favorable Kozak context occurs position 27, however an upstream in-frame stop site is not present. To identify cDNA clones extending further 5', human heart and fetal retina libraries were screened with the tpr2a derived 1.2 kb probe, C (shown in FIG. 1). Three cDNAs, none of which extended beyond the 5'sequence present in tpr1 were identified. A composite sequence derived from these clones and from tpr2a and b encodes a predicted protein of 483 aa from the putative methionine to the stop codon (FIGS. 3A–B). A BLAST search of the NCBI databases revealed that tpr2 contains seven TPR motifs.

tpr1 and tpr2 TPR units were aligned with a consensus TPR sequence. Quantitative sequence comparisons have shown that several classes of TPR sequences exist (Sikorski, R. S. et al., "TPR proteins as essential components of the yeast cell cycle," in *Cold Spring Harbor Symp. Quant. Biol.* LVI (1991), pp. 663–673). Class I TPRs consist only of the TPR sequences found in the Drosophila crooked neck (cm protein) (Zhang, K et al, *Genes. Dev.* 5:1080 (1991)). The TPRs of several proteins with cell cycle related functions (e.g., cdc23 and nuc2) are similar to one another and have been classified as class 11 TPRs. The tpr1 and 2 repeats are highly related to one another and are most similar to TPR units found in class III TPR family members such as p58, STI1, IEF SSP 3521, MAS and MOM. These proteins have diverse functions that are not directly related to cell cycling and include the antiviral interferon response, the stress response and protein import.

Interestingly, just downstream of the TPR repeats, tpr2 contains a 69 amino acid stretch that is significantly similar (45%–56% identity) (Lee, T. G. et et al., *Mol. Cell. Biol.* 14:2331–2342 (1994); Narberhaus, F. et al., *J. Bacteriol.* 174:3290–3299 (1992)) to a highly conserved ~70 amino acid region, the "Jregion" found in all members of the DnaJ protein family. In bacteria, DnaJ is thought to function with DnaK (the hsp 70 equivalent of *E. coli*) in a variety of reactions involving protein folding and it has been suggested that the "J region" mediates their interaction (Silver & Way, *Cell* 74:5–6 (1993)). Several eukaryotic genes related to part or all of DnaJ have been identified and it has been proposed that their encoded proteins direct the activity of HSP70 to different substrates (Cheetam, M. E. et al., *Biochem. J.* 284:469–476 (1992); Cyr, D. M. et al., *J. Biol. Chem.* 267:20927–20931 (1992); Sadler, I. et al., *J. Cell. Biol.* 109(6):2665–2675 (1989)). Indeed, one of these proteins, p58, is structurally related to tpr2 in that it also contains tandem arrays of TPR motifs (in this case, 9) upstream of a DnaJ sequence. P58 was originally identified as a negative regulator of PKR, a serine/threonine kinase induced by interferon treatment and activated by double stranded RNAs (Narberhaus, F. et al., *J. Bacteriol.* 174:3290–3299 (1992)). A comparison of the bovine p58 coding sequence (Lee, T. G. et al., *Mol. Cell. Biol.* 14:2331–2342 (1994)) with the predicted tpr2 protein reveals a high degree of amino acid similarity (48% similarity; 30% identity) extending linearly from the first TPR unit through the DnaJ similarity region. This level of conservation implies that while tpr2 is probably not a human homologue of p58 it is very likely a closely related family member. Indeed, the conservation of the placement of TPR units is particularly striking. The analysis of the tpr2 predicted protein revealed the 7 TPR units shown (TPR units were identified by comparison with known TPR-contaning proteins and with the general TPR consensus . . . W . . . LGY . . . A . . . F . . . A . . . P . . . (Sikorski, R. S. et al., "TPR proteins as essential components of the yeast cell cycle," in *Cold Spring Harbor Symp. Quant. Biol.* LVI (1991), pp. 663–673) but did not identify TPRs analogous to the fourth and fifth TPR units of p58. However, because of the degenerate nature of these repeats it is possible that the region between the third and fourth TPR units of tpr2 may encode sequences evolved from TPRS. This comparison with p58 also supports initiation of translation at the first ATG in tpr2. The tpr2 protein is predicted to be mainly hydrophilic with a hydrophobic region located at the predicted amino terminus (amino acids 1–15).

Example 4

Chromosomal Mapping

To determine the chromosomal locations of the tpr1 and tpr2 genes in humans, a panel of 43 human-rodent hybrid DNAs containing defined overlapping subsets of human chromosomes (Geisslar, E. N. et al., *Somatic Cell Genetics* 17:207–214 (1991); Pelletier, J. et al., *Genomics* 10:1079–1082 (1991)) and NIGMS Mapping panel #2 (Coriell Institute, Camden, N.J.) were hybridized with the tpr1B and tpr2a C probes shown in FIG. 1.

As shown in a representative panel (FIG. 4A), the tpr1 probe detects a single EcoRI fragment in the total human and the HHW599 (chromosome 5 hybrid) lines, suggesting that this gene is unique and that it maps to human chromosome 5. To regionally localize tpr1, a chromosome 5 deletion panel was screened by PCR with the synthetic oligonucleotide primers tpr1b and tpr1c (FIG. 4B). The expected 400 bp product could be mapped to 5q32–33.2 based on its amplification in HHW 1600 which contains human chromosome 5 sequences extending from the qter to 5q32 and HHW 1138 which contains sequences from Spter to 5q33.2 (Warrington, J. A. et al., *Genomics* 11:701–708 (1991)).

The tpr2a C probe detects a more complicated pattern of bands in total human DNA (FIG. 5A). A strongly hybridizing subset of these bands (illustrated in FIG. 5A by filled in arrows) is present only in the chromosome 17 containing hybrids. Two bands with weaker hybridization signal do not map to chromosome 17 suggesting the existence of related sequences, but these could not be assigned unequivocally to another chromosome using this panel. It is unlikely that the weak bands represent hybridization with TPR elements in an otherwise unrelated gene since TPR motifs are highly degenerate even at the protein level. Indeed, the tpr1 and tpr2 cDNAs do not crosshybridize detectably. To sublocalize the tpr2 sequences on chromosome 17 use of a regional mapping panel was made(FIG. 5B). The results show that the tpr2 chromosome 17 specific bands are apparent in JW-4, LS1, SP3, DCR-1, and NF13 but are not detectable in MH41 indicating that tpr2 maps to 17q11.2–23 distal to NF1 (at 17q11.2).

Example 5 mRNA Expression

To determine the pattern of tpr1 and tpr2 mRNA expression, the tpr1B and tpr2a C probes were sequentially hybridized to Northern blots of polyA+ RNA derived from a variety of adult and fetal primary tissues (FIG. 6). A panel probed with α-actin is shown as a control for the amount of RNA loaded. The tpr1 probe detects a 1.6 kb transcript that appears to be ubiquitously expressed in adult and fetal tissues. Distinct ~1.3 kb and ~1.2 kb species are also detected at lower levels in adult heart and testis, respectively, but neither is detectable in any other tissue tested. The tpr2 probe detects a single transcript of 2.2 kb, expressed ubiquitously.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A substantially pure polypeptide comprising the tpr1 amino acid sequence set forth in SEQ ID NO:2.

2. An isolated nucleic acid molecule encoding the polypeptide of claim 1.

3. The isolated nucleic acid molecule according to claim 2, wherein the molecule comprises the nucleic acid sequence set forth in SEQ ID NO:1 which encodes the amino acid sequence set forth in SEQ ID NO:2.

4. A recombinant nucleic acid molecule comprising, 5' to 3', a promoter effective to initiate transcription in a host cell and the isolated nucleic acid molecule according to claim 2.

5. A recombinant nucleic acid molecule comprising a vector and the isolated nucleic acid molecule according to claim 2.

6. A cell that is transformed with the recombinant nucleic acid molecule according to claim 4.

7. A substantially pure polypeptide comprising the tpr2 amino acid sequence set forth in SEQ ID NO:4.

8. An isolated nucleic acid molecule encoding the polypeptide of claim 7.

9. The isolated nucleic acid molecule according to claim 8, wherein the molecule comprises the nucleic acid sequence set fort in SEQ ID NO:3 which encodes the amino acid sequence set forth in SEQ ID NO:4.

10. A recombinant nucleic acid molecule comprising, 5' to 3', a promoter effective to initiate transcription in a host cell and the isolated nucleic acid molecule according to claim 8.

11. A recombinant nucleic acid molecule comprising a vector and the isolated nucleic acid molecule according to claim 8.

12. cell that is transformed with the recombinant nucleic acid molecule according to claim 10.

\* \* \* \* \*